United States Patent [19]
Göres et al.

[11] Patent Number: 5,892,078
[45] Date of Patent: Apr. 6, 1999

[54] STEREORIGID METALLOCENE COMPOUND

[75] Inventors: Markus Göres, Eschborn; Frank Küber, Oberursel; Berthold Schiemenz, Frankfurt, all of Germany

[73] Assignee: Targor GmbH, Germany

[21] Appl. No.: 949,790

[22] Filed: Oct. 14, 1997

[30] Foreign Application Priority Data

Oct. 15, 1996 [DE] Germany .................. 196 42 432.1
May 6, 1997 [DE] Germany .................. 197 19 104.5

[51] Int. Cl.$^6$ ............... C07F 17/00; C07F 7/28; C07F 11/00

[52] U.S. Cl. ................. 556/41; 556/12; 556/20; 556/28; 556/43; 556/53; 556/58; 556/54; 502/103; 502/117; 526/160; 526/943

[58] Field of Search ................. 556/11, 12, 20, 556/28, 43, 53, 54, 58; 502/103, 117; 526/160, 943

[56] References Cited

U.S. PATENT DOCUMENTS 5,710,297 1/1998 Weller et al. .................. 556/11

*Primary Examiner*—Porfirio Nazario-Gonzalez
*Attorney, Agent, or Firm*—Connolly & Hutz

[57] ABSTRACT

The present invention relates to a stereorigid metallocene compound which has as ligands at least two substituted or unsubstituted cyclopentadienyl groups which are connected to one another via a five-membered ring, where at least one cyclopentadienyl group is fuzed to the five-membered ring and the ligand system of the stereorigid metallocene compound is different from 4-[($\eta^5$-3'-alkyl-cyclopentadienyl)-4,6,6-trimethyl-($\eta^5$-2-alkyl-4,5-tetrahydropentalene)]. The metallocene compound of the invention is suitable as a catalyst component for olefin polymerization.

9 Claims, No Drawings

STEREORIGID METALLOCENE COMPOUND

The present invention relates to a specific stereorigid metallocene compound and also a process for preparing polyolefins in the presence of this specific stereorigid metallocene compound.

The preparation of polyolefins using soluble metallocene compounds in combination with aluminoxanes or other cocatalysts which, owing to their Lewis acidity, can convert the neutral metallocene into a cation and stabilize it are known from the literature (EP 129 368, EP 351 392).

The proceedings of the 1st Journal of Organometallic Chemistry Conference on Applied Organometallic Chemistry, page 136 describes metallocenes which have a substituted tricyclic hydrocarbon as ligand system.

The use of soluble metallocene compounds based on bis(cyclopentadienyl)dialkylzirconium or bis(cyclopentadienyl)zirconium dihalide in combination with oligomeric aluminoxanes gives atactic polymers which, owing to their unbalanced and unsatisfactory product properties, are of little industrial importance. In addition, certain olefin copolymers are not obtainable.

Derivatives of zirconocene dichloride in which the two substituted cyclopentadienyl groups are connected to one another via a methylene, ethylene or dimethylsilylene bridge can, owing to their conformational rigidity, be used as catalysts for the isospecific polymerization of olefins (Chem. Lett. 1989, pp. 1853–1856 or EP-A 0 316 155). Metallocenes having (substituted) indenyl radicals as ligands are of particular importance for preparing highly isotactic polymers having a high crystallinity and a high melting point (EP 485 823, EP 530 647).

Polyolefins whose property profile lies between these two extremes are also of great interest.

It is an object of the invention to provide a metallocene compound which avoids the disadvantages of the prior art and is suitable for preparing polyolefins.

The present invention accordingly provides a stereorigid metallocene compound of the formula I

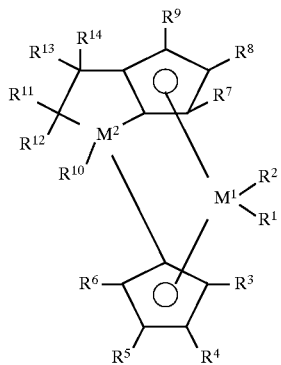

(I)

where $M^1$ is a metal of group IIIb, IVb, Vb or VIb of the Periodic Table, $M^2$ is carbon, silicon or germanium, $R^1$ and $R^2$ are identical or different and are each a hydrogen atom, a $C_1$–$C_{40}$-group such as a $C_1$–$C_{10}$-alkyl, $C_1$–$C_{10}$-alkoxy, $C_6$–$C_{10}$-aryl, $C_6$–$C_{25}$-aryloxy, $C_2$–$C_{10}$-alkenyl, $C_7$–$C_{40}$-arylalkyl or $C_7$–$C_{40}$-arylalkenyl group, an OH group, a halogen atom or $NR^{15}_2$, where $R^{15}$ is a halogen atom, a $C_1$–$C_{10}$-alkyl group or a $C_6$–$C_{10}$-aryl group, or $R^1$ and $R^2$ together with the atoms connecting them form a ring system, $R^3$, $R^4$, $R^5$, $R6$, $R^7$, $R^8$ and $R^9$ are identical or different and are each a hydrogen atom, a halogen atom, a $C_1$–$C_{40}$-group such as a $C_1$–$C_{10}$-alkyl group which may be halogenated, a $C_6$–$C_{30}$-aryl group which may be halogenated, a $C_6$–$C_{20}$-aryloxy, $C_2$–$C_{12}$-alkenyl, $C_7$–$C_{40}$-arylalkyl, $C_7$–$C_{40}$-alkylaryl or $C_8$–$C_{40}$-arylalkenyl group, an —$SiR^{15}_3$, —$NR^{15}_2$, —$SiOR^{15}_3$, —$SiSR^{15}_3$ or —$PR^{15}_2$ radical, where $R^{15}$ are identical or different and are each a halogen atom, a $C_1$–$C_{10}$-alkyl group or a $C_6$–$C_{10}$-aryl group or form a ring system, or two or more adjacent radicals $R^3$, $R^4$, $R^5$, $R^6$, $R^7$, $R^8$ and $R^9$ together with the atoms connecting them form a ring system which preferably contains from 4 to 40, particularly preferably from 6 to 20, carbon atoms, $R^{10}$, $R^{13}$ and $R^{14}$ are identical or different, preferably identical, and are each a $C_1$–$C_{20}$-alkyl group, $R^{11}$ and $R^{12}$ are identical or different and are each a hydrogen atom, a $C_1$–$C_{40}$-group such as a $C_1$–$C_{20}$-alkyl, $C_1$–$C_{10}$-alkoxy, $C_6$–$C_{20}$-aryl, $C_2$–$C_{12}$-alkenyl, $C_7$–$C_{40}$-arylalkyl, $C_7$–$C_{40}$-alkylaryl or $C_8$–$C_{40}$-arylalkenyl group, each of which may bear radicals such as a halogen atom, —$NR^{15}_3$, —$SR^{15}_2$, —$SiR^{15}_3$ or —$OSiR^{15}_3$, where $R^{15}$ is a halogen atom, a $C_1$–$C_{10}$-alkyl group or a $C_6$–$C_{10}$-aryl group, and the ligand system of the compound of the formula I is different from 4-($\eta^5$-3'-alkylcyclopentadienyl)-4,6,6-trimethyl-($\eta^5$-2-alkyl-4,5-tetrahydropentalene). When $M^2$ is carbon and $R^{10}$, $R^{13}$ and $R^{14}$ are methyl, it is preferred that at least one of the radicals $R^3$, $R^5$, $R^6$, $R^7$ and $R^9$ is not hydrogen and/or $R^8$ is hydrogen. The $C_1$–$C_{20}$-alkyl groups $R^{10}$, $R^{13}$ and $R^{14}$ can be unbranched or branched.

In compounds of the formula I it is preferred that $M^1$ is a metal of group IVb of the Periodic Table of the Elements, for example titanium, zirconium or hafnium, in particular zirconium, $R^1$ and $R^2$ are identical and are each a $C_1$–$C_4$-alkyl group or a halogen atom such as fluorine, chlorine, bromine or iodine, in particular chlorine, $R^3$, $R^4$, $R^5$, $R^6$, $R^7$, $R^8$ and $R^9$ are identical or different and are each a hydrogen atom, a $C_1$–$C_{10}$-alkyl group or a $C_6$–$C_{24}$-aryl group, or two or more adjacent radicals $R^3$, $R^4$, $R^5$, $R^6$, $R^7$, $R^8$ and $R^9$ together with the atoms connecting them form an aromatic or aliphatic ring system having from 4 to 20 carbon atoms, $R^{10}$, $R^{13}$ and $R^{14}$ are each a $C_1$–$C_{10}$-alkyl group, in particular a $C_1$–$C_6$-alkyl group, $M^2$ is carbon, $R^{11}$ and $R^{12}$ are identical or different and $R^{11}$ is a hydrogen atom, a $C_1$–$C_{10}$-group, in particular a $C_1$–$C_4$-alkyl group or a $C_6$–$C_{10}$-aryl group, and $R^{12}$ is a hydrogen atom and at least one of the radicals $R^3$, $R^5$, $R^6$, $R^7$ and $R^9$ is not hydrogen and/or $R^8$ is hydrogen.

Particular preference is given to compounds of the formula I in which $M^1$ is zirconium, $R^1$ and $R^2$ are identical and are each a halogen atom, in particular chlorine, $R^3$, $R^4$, $R^5$, $R^6$, $R^7$ and $R^9$ are identical or different and are each a hydrogen atom or a $C_1$–$C_4$-alkyl group such as methyl, ethyl, propyl, isopropyl, butyl, t-butyl or isobutyl or a $C_6$–$C_{14}$-aryl group such as phenyl or naphthyl, $R^3$ and $R^4$ and/or $R^5$ and $R^6$ together with the atoms connecting them form an aromatic hydrocarbon ring system having from 4 to 20 carbon atoms, in particular a 6-membered ring which may in turn be substituted, $R^8$ is a hydrogen atom, $M^2$ is a carbon atom, $R^{10}$, $R^{13}$ and $R^{14}$ are each a $C_1$–$C_6$-alkyl group such as methyl, ethyl, propyl, isopropyl, butyl, isobutyl, tert-butyl or hexyl, in particular methyl, $R^{11}$ and $R^{12}$ are identical and are each a hydrogen atom.

EXAMPLES OF METALLOCENE COMPOUNDS ACCORDING TO THE INVENTION ARE:

[4-($\eta^5$-cyclopentadienyl)-4,6,6-trimethyl-($\eta^5$-4,5-tetrahydropentalene)]-dichlorotitanium

[4-($\eta^5$-cyclopentadienyl)-4,6,6-trimethyl-($\eta^5$-4,5-tetrahydropentalene)]-dichlorozirconium

[4-($\eta^5$-cyclopentadienyl)-4,6,6-trimethyl-($\eta^5$-4,5-tetrahydropentalene)]-dichlorohafnium

[4-($\eta^5$-3'-methylcyclopentadienyl)-4,6,6-trimethyl-($\eta^5$-4,5-tetrahydropentalene)]dichlorozirconium

[4-($\eta^5$-3'-ethylcyclopentadienyl)-4,6,6,-trimethyl-($\eta^5$-4,5-tetrahydropentalene)]dichlorozirconium

[4-($\eta^5$-3'-isopropylcyclopentadienyl)-4,6,6-trimethyl-($\eta^5$-4,5-tetrahydropentalene)]dichlorozirconium

[4-($\eta^5$-3'-isobutylcyclopentadienyl)-4,6,6-trimethyl-($\eta^5$-4,5-tetrahydropentalene)]dichlorozirconium

[4-($\eta^5$-3'-cyclohexylcyclopentadienyl)-4,6,6-trimethyl-($\eta^5$-4,5-tetrahydropentalene)]dichlorozirconium

[4-($\eta^5$-3'-tert-butylcyclopentadienyl)-4,6,6-trimethyl-($\eta^5$-4,5-tetrahydropentalene)]dichlorozirconium

[4-($\eta^5$-3'-benzylcyclopentadienyl)-4,6,6-trimethyl-($\eta^5$-4,5-tetrahydropentalene)]dichlorozirconium

[4-($\eta^5$-3'-phenylcyclopentadienyl)-4,6,6-trimethyl-($\eta^5$-4,5-tetrahydropentalene)]dichlorozirconium

[4-($\eta^5$-3'-trimethylsilylcyclopentadienyl)-4,6,6-trimethyl-($\eta^5$-4,5-tetrahydropentalene)]dichlorozirconium

[4-($\eta^5$-3'-methyl-5'-methylcyclopentadienyl)-4,6,6-trimethyl-($\eta^5$-4,5-tetrahydropentalene]dichlorozirconium

[4-($\eta^5$-3'-ethyl-5'-methylcyclopentadienyl)-4,6,6-trimethyl-($\eta^5$-4,5-tetrahydropentalene)]dichlorozirconium

[4-($\eta^5$-3'-isopropyl-5'-methylcyclopentadienyl)-4,6,6-trimethyl-($\eta^5$-4,5-tetrahydropentalene)]dichlorozirconium

[4-($\eta^5$-3'-tert-butyl-5'-methylcyclopentadienyl)-4,6,6-trimethyl-($\eta^5$-4,5-tetrahydropentalene)]dichlorozirconium

[4-($\eta^5$-3'-benzyl-5'-methylcyclopentadienyl)-4,6,6-trimethyl-($\eta^5$-4,5 -tetrahydropentalene]dichlorozirconium

[4-($\eta^5$-3'-phenyl-5'-methylcyclopentadienyl)-4,6,6-trimethyl-($\eta^5$-4,5-tetrahydropentalene)]dichlorozirconium

[4-($\eta^5$-3'-methyl-5'-ethylcyclopentadienyl)-4,6,6-trimethyl-($\eta^5$-4,5-tetrahydropentalene)]dichlorozirconium

[4-($\eta^5$-3'-ethyl-5'-ethylcyclopentadienyl)-4,6,6-trimethyl-($\eta^5$-4,5-tetrahydropentalene)]dichlorozirconium

[4-($\eta^5$-3'-isopropyl-5'-ethylcyclopentadienyl)-4,6,6-trimethyl-($\eta^5$-4,5-tetrahydropentalene)]dichlorozirconium

[4-($\eta^5$-3'-tert-butyl-5'-ethylcyclopentadienyl)-4,6,6-trimethyl-($\eta^5$-4,5-tetrahydropentalene)]dichlorozirconium

[4-($\eta^5$-3'-benzyl-5'-ethylcyclopentadienyl)-4,6,6-trimethyl-($\eta^5$-4,5-tetrahydropentalene)]dichlorozirconium

[4-($\eta^5$-3'-phenyl-5'-ethylcyclopentadienyl)-4,6,6-trimethyl-($\eta^5$-4,5 -tetrahydropentalene)]dichlorozirconium

[4-($\eta^5$-3'-methyl-5'-isopropylcyclopentadienyl)-4,6,6-trimethyl-($\eta^5$-4,5-tetrahydropentalene)]dichlorozirconium

[4-($\eta^5$-3'-ethyl-5'-isopropylcyclopentadienyl)-4,6,6-trimethyl-($\eta^5$-4,5-tetrahydropentalene)]dichlorozirconium

[4-($\eta^5$-3'-isopropyl-5'-isopropylcyclopentadienyl)-4,6,6-trimethyl-($\eta^5$-4,5-tetrahydropentalene)]dichlorozirconium

[4-($\eta^5$-3'-tert-butyl-5'-isopropylcyclopentadienyl)-4,6,6-trimethyl-($\eta^5$-4,5-tetrahydropentalene)]dichlorozirconium

[4-($\eta^5$-3'-benzyl-5'-isopropylcyclopentadienyl)-4,6,6-trimethyl-($\eta^5$-4,5-tetrahydropentalene)]dichlorozirconium

[4-($\eta^5$-3'-phenyl-5'-isopropylcyclopentadienyl)-4,6,6-trimethyl-($\eta^5$-4,5-tetrahydropentalene)]dichlorozirconium

[4-($\eta^5$-cyclopentadienyl)-4,6,6-triethyl-($\eta^5$-4,5-tetrahydropentalene)]dichlorozirconium

[4-($\eta^5$-3'-methylcyclopentadienyl)-4,6,6-triethyl-($\eta^5$-4,5-tetrahydropentalene)]dichlorozirconium

[4-($\eta^5$-3'-ethylcyclopentadienyl)-4,6,6-triethyl-($\eta^5$-4,5-tetrahydropentalene)]dichlorozirconium

[4-($\eta^5$-3'-isopropylcyclopentadienyl)-4,6,6,-triethyl-($\eta^5$-4,5-tetrahydropentalene)]dichlorozirconium

[4-($\eta^5$-3'-isobutylcyclopentadienyl)-4,6,6-triethyl-($\eta^5$-4,5-tetrahydropentalene)]dichlorozirconium

[4-($\eta^5$-3'-cyclohexylcyclopentadienyl)-4,6,6-triethyl-($\eta^5$-4,5-tetrahydropentalene)]dichlorozirconium

[4-($\eta^5$-3'-tert-butylcyclopentadienyl)-4,6,6-triethyl-($\eta^5$-4,5-tetrahydropentalene)]dichlorozirconium

[4-($\eta^5$-3'-benzylcyclopentadienyl)-4,6,6-triethyl-($\eta^5$-4,5-tetrahydropentalene)]dichlorozirconium

[4-($\eta^5$-3'-phenylcyclopentadienyl)-4,6,6-triethyl-($\eta^5$-4,5-tetrahydropentalene)]dichlorozirconium

[4-($\eta^5$-cyclopentadienyl)-4-methyl-6,6-diethyl-($\eta^5$-4,5-tetrahydropentalene)]dichlorozirconium

[4-($\eta^5$-3'-methylcyclopentadienyl)-4-methyl-6,6-diethyl-($\eta^5$-4,5-tetrahydropentalene)]dichlorozirconium

[4-($\eta^5$-3'-ethylcyclopentadienyl)-4-methyl-6,6-diethyl-($\eta^5$-4,5-tetrahydropentalene)]dichlorozirconium

[4-($\eta^5$-3'-isopropylcyclopentadienyl)-4-methyl-6,6-diethyl-($\eta^5$-4,5-tetrahydropentalene)]dichlorozirconium

[4-($\eta^5$-3'-benzylcyclopentadienyl)-4-methyl-6,6-diethyl-($\eta^5$-4,5-tetrahydropentalene)]dichlorozirconium

[4-($\eta^5$-3'-phenylcyclopentadienyl)-4-methyl-6,6-diethyl-($\eta^5$-4,5-tetrahydropentalene)]dichlorozirconium

[4-($\eta^5$-3'-cyclopentadienyl)-4-ethyl-6,6-dimethyl-($\eta^5$-4,5-tetrahydropentalene)]dichlorozirconium

[4-($\eta^5$-3'-methylcyclopentadienyl)-4-ethyl-6,6-dimethyl-($\eta^5$-4,5-tetrahydropentalene)]dichlorozirconium

[4-($\eta^5$-3'-ethylcyclopentadienyl)-4-ethyl-6,6-dimethyl-($\eta^5$-4,5-tetrahydropentalene)]dichlorozirconium

[4-($\eta^5$-3'-isopropylcyclopentadienyl)-4-ethyl-6,6-dimethyl-($\eta^5$-4,5-tetrahydropentalene)]dichlorozirconium

[4-($\eta^5$-3'-benzylcyclopentadienyl)-4-ethyl-6,6-dimethyl-($\eta^5$-4,5-tetrahydropentalene)]dichlorozirconium

[4-($\eta^5$-3'-phenylcyclopentadienyl)-4-ethyl-6,6-dimethyl-($\eta^5$-4,5-tetrahydropentalene)]dichlorozirconium

[4-($\eta^5$-cyclopentadienyl)-4-methyl-6-ethyl-6-methyl-($\eta^5$-4,5-tetrahydropentalene)]dichlorozirconium

[4-($\eta^5$-3'-methylcyclopentadienyl)-4-methyl-6-ethyl-6-methyl-($\eta^5$-4,5-tetrahydropentalene)]dichlorozirconium

[4-($\eta^5$-3'-ethylcyclopentadienyl)-4-methyl-6-ethyl-6-methyl-($\eta^5$-4,5-tetrahydropentalene)]dichlorozirconium

[4-($\eta^5$-3'-isopropylcyclopentadienyl)-4-methyl-6-ethyl-6-methyl-($\eta^5$-4,5 -tetrahydropentalene)]dichlorozirconium

[4-($\eta^5$-3'-benzylcyclopentadienyl)-4-methyl-6-ethyl-6-methyl-($\eta^5$-4,5-tetrahydropentalene)]dichlorozirconium

[4-($\eta^5$-3'-phenylcyclopentadienyl)-4-methyl-6-ethyl-6-methyl-($\eta^5$-4,5-tetrahydropentalene)]dichlorozirconium

[4-($\eta^5$-cyclopentadienyl)-4-methyl-6-isopropyl-6-methyl-($\eta^5$-4,5-tetrahydropentalene)]dichlorozirconium

[4-($\eta^5$-3'-methylcyclopentadienyl)-4-methyl-6-isopropyl-6-methyl-($\eta^5$-4,5-tetrahydropentalene)]dichlorozirconium

[4-($\eta^5$-3'-ethylcyclopentadienyl)-4-methyl-6-isopropyl-6-methyl-($\eta^5$-4,5-tetrahydropentalene)]dichlorozirconium

[4-($\eta^5$-3'-isopropylcyclopentadienyl)-4-methyl-6-isopropyl-6-methyl-($\eta^5$-4,5-tetrahydropentalene)]dichlorozirconium

[4-($\eta^5$-3'-benzylcyclopentadienyl)-4-methyl-6-isopropyl-6-methyl-($\eta^5$-4,5-tetrahydropentalene)]dichlorozirconium

[4-($\eta^5$-3'-phenylcyclopentadienyl)-4-methyl-6-isopropyl-6-methyl-($\eta^5$-4,5-tetrahydropentalene)]dichlorozirconium

[4-($\eta^5$-3'-trimethylsilyl-5'-ethylcyclopentadienyl)-4,6,6-trimethyl-($\eta^5$-4,5-tetrahydropentalene)]dichlorozirconium

[4-($\eta^5$-3'-trimethylsilyl-5'-isopropylcyclopentadienyl)-4,6,6-trimethyl-($\eta^5$-4,5-tetrahydropentalene)]dichlorozirconium

[4-($\eta^5$-3'-trimethylsilylcyclopentadienyl)-4,6,6-triethyl-($\eta^5$-4,5-tetrahydropentalene)]dichlorozirconium

[4-($\eta^5$-3'-trimethylsilylcyclopentadienyl)-4-methyl-6,6-diethyl-($\eta^5$-4,5-tetrahydropentalene)]dichlorozirconium

[4-($\eta^5$-3'-trimethylsilylcyclopentadienyl)-4-ethyl-6,6-dimethyl-($\eta^5$-4,5-tetrahydropentalene)]dichlorozirconium

[4-($\eta^5$-3'-trimethylsilylcyclopentadienyl)-4-methyl-6-ethyl-6-methyl-($\eta^5$-4,5-tetrahydropentalene)]dichlorozirconium

[4-($\eta^5$-3'-trimethylsilylcyclopentadienyl)-4-methyl-6-isopropyl-6-methyl-($\eta^5$-4,5-tetrahydropentalene)]dichlorozirconium

[4-($\eta^5$-fluorenyl)-2,4,6,6-tetramethyl-$\eta^5$-tetrahydropentalene]dichlorozirconium

[4-($\eta^5$-fluorenyl)-2,4,6,6-tetramethyl-$\eta^5$-tetrahydropentalene]dichlorotitanium

[4-($\eta^5$-fluorenyl)-2,4,6,6-tetramethyl-$\eta^5$-tetrahydropentalene]dichlorohafnium

[4-($\eta^5$-fluorenyl)-2,4,6,6-tetramethyl-$\eta^5$-tetrahydropentalene]bis(diethylamino)zirconium

[4-($\eta^5$-fluorenyl)-2,4,6,6-tetramethyl-$\eta^5$-tetrahydropentalene]bis(dimethylamino)zirconium

[4-($\eta^5$-fluorenyl)-4,6,6-trimethyl-(2-ethyl)-$\eta^5$-tetrahydropentalene]-dichlorozirconium

[4-($\eta^5$-fluorenyl)-4,6,6-trimethyl-(2-isopropyl)-$\eta^5$-tetrahydropentalene]dichlorozirconium

[4-($\eta^5$-fluorenyl)-4,6,6-trimethyl-(2-benzyl)-$\eta^5$-tetrahydropentalene]dichlorozirconium

[4-($\eta^5$-fluorenyl)-4,6,6-trimethyl-(2-trimethylsilyl)-$\eta^5$-tetrahydropentalene]dichlorozirconium

[4-($\eta^5$-indenyl)-2,4,6,6-tetramethyl-$\eta^5$-tetrahydropentalene]dichlorozirconium

[4-($\eta^5$-indenyl)-2,4,6,6-tetramethyl-$\eta^5$-tetrahydropentalene]dichlorotitanium

[4-($\eta^5$-indenyl)-2,4,6,6-tetramethyl-$\eta^5$-tetrahydropentalene]dichlorohafnium

[4-($\eta^5$-indenyl)-2,4,6,6-tetramethyl-$\eta^5$-tetrahydropentalene]bis(diethylamino)zirconium

[4-($\eta^5$-indenyl)-2,4,6,6-tetramethyl-$\eta^5$-tetrahydropentalene]bis(dimethylamino)zirconium

[4-($\eta^5$-indenyl)-4,6,6-trimethyl-(2-ethyl)-$\eta^5$-tetrahydropentalene]dichlorozirconium

[4-($\eta^5$-indenyl)-4,6,6-trimethyl-(2-isopropyl)-$\eta^5$-tetrahydropentalene]dichlorozirconium

[4-($\eta^5$-indenyl)-4,6,6-trimethyl-(2-benzyl)-$\eta^5$-tetrahydropentalene]dichlorozirconium

[4-($\eta^5$-indenyl)-4,6,6-trimethyl-(2-trimethylsilyl)-$\eta^5$-tetrahydropentalene]dichlorozirconium

[4-($\eta^5$-2-methylindenyl)-2,4,6,6-tetramethyl-$\eta^5$-tetrahydropentalene]-dichlorozirconium

[4-($\eta^5$-2-methylindenyl)-2,4,6,6-tetramethyl-$\eta^5$-tetrahydropentalene]-dichlorotitanium

[4-($\eta^5$-2-methylindenyl)-2,4,6,6-tetramethyl-$\eta^5$-tetrahydropentalene]-dichlorohafnium

[4-($\eta^5$-2-methylindenyl)-2,4,6,6-tetramethyl-$\eta^5$-tetrahydropentalene]bis(diethylamino)zirconium

[4-($\eta^5$-2-methylindenyl)-2,4,6,6-tetramethyl-$\eta^5$-tetrahydropentalene]bis(diethylamino)zirconium

[4-($\eta^5$-2-methylindenyl)-4,6,6-trimethyl-(2-ethyl)-$\eta^5$-tetrahydropentalene]dichlorozirconium

[4-($\eta^5$-2-methylindenyl)-4,6,6-trimethyl-(2-isopropyl)-$\eta^5$-tetrahydropentalene]dichlorozirconium

[4-($\eta^5$-2-methylindenyl)-4,6,6-trimethyl-(2-benzyl)-$\eta^5$-tetrahydropentalene]dichlorozirconium

[4-($\eta^5$-2-methylindenyl)-4,6,6-trimethyl-(2-trimethysilyl)-$\eta^5$-tetrahydropentalene]dichlorozirconium

[4-($\eta^5$-benzoindenyl)-2,4,6,6-tetramethyl-$\eta^5$-tetrahydropentalene]dichlorozirconium

[4-($\eta^5$-benzoindenyl)-2,4,6,6-tetramethyl-$\eta^5$-tetrahydropentalene]dichlorotitanium

[4-($\eta^5$-benzoindenyl)-2,4,6,6-tetramethyl-$\eta^5$-tetrahydropentalene]dichlorohafnium

[4-($\eta^5$-benzoindenyl)-2,4,6,6-tetramethyl-$\eta^5$-tetrahydropentalene]bis(diethylamino)zirconium

[4-($\eta^5$-benzoindenyl)-2,4,6,6-tetramethyl-$\eta^5$-tetrahydropentalene]bis(dimethylamino)zirconium

[4-($\eta^5$-benzoindenyl)-4,6,6-trimethyl(2-ethyl)-$\eta^5$-tetrahydropentalene]dichlorozirconium

[4-($\eta^5$-benzoindenyl)-4,6,6-trimethyl-(2-isopropyl)-$\eta^5$-tetrahydropentalene]dichlorozirconium

[4-($\eta^5$-benzoindenyl)-4,6,6-trimethyl(2-benzyl)-$\eta^5$-tetrahydropentalene]dichlorozirconium

[4-($\eta^5$-benzoindenyl)-4,6,6-trimethyl-(2-trimethylsilyl)-$\eta^5$-tetrahydropentalene]dichlorozirconium

[4-($\eta^5$-cyclopentadienyl)-2,4,6,6-tetramethyl-$\eta^5$-tetrahydropentalene]-dichlorozirconium

[4-($\eta^5$-cyclopentadienyl)-2,4,6,6-tetramethyl-$\eta^5$-tetrahydropentalene]-dichlorotitanium

[4-($\eta^5$-cyclopentadienyl)-2,4,6,6-tetramethyl-$\eta^5$-tetrahydropentalene]-dichlorohafnium

[4-($\eta^5$-cyclopentadienyl)-2,4,6,6-tetramethyl-$\eta^5$-tetrahydropentalene]-bis(diethylamino)zirconium

[4-($\eta^5$-cyclopentadienyl)-2,4,6,6-tetramethyl-$\eta^5$-tetrahydropentalene]-bis(dimethylamino)zirconium

[4-($\eta^5$-cyclopentadienyl)-4,6,6-trimethyl-(2-ethyl)-$\eta^5$-tetrahydropentalene]-dichlorozirconium

[4-($\eta^5$-cyclopentadienyl)-4,6,6-trimethyl-(2-isopropyl)-$\eta^5$-tetrahydropentalene]-dichlorozirconium

[4-($\eta^5$-cyclopentadienyl)-4,6,6-trimethyl-(2-benzyl)-$\eta^5$-tetrahydropentalene]-dichlorozirconium

[4-($\eta^5$-cyclopentadienyl)-4,6,6-trimethyl-(2-trimethylsilyl)-$\eta^5$-tetrahydropentalene]dichlorozirconium

[4-($\eta^5$-fluorenyl)-2,4-dimethyl-6-phenyl-($\eta^5$-4,5-tetrahydropentalene)]-dichlorozirconium

[4-($\eta^5$-fluorenyl)-2-ethyl-4-methyl-6-phenyl-($\eta^5$-4,5-tetrahydropentalene)]dichlorozirconium

[4-($\eta^5$-fluorenyl)-2-isopropyl-4-methyl-6-phenyl-($\eta^5$-4,5-tetrahydropentalene)]dichlorozirconium

[4-($\eta^5$-fluorenyl)-2-tert-butyl-4-methyl-6-phenyl-($\eta^5$-4,5-tetrahydropentalene)]dichlorozirconium

[4-($\eta^5$-fluorenyl)-2-benzyl-4-methyl-6-phenyl-($\eta^5$-4,5-tetrahydropentalene)]dichlorozirconium

[4-($\eta^5$-fluorenyl)-2-trimethylsilyl-4-methyl-6-phenyl-($\eta^5$-4,5-tetrahydropentalene)]dichlorozirconium

[4-(η⁵-fluorenyl)-2-dimethyl-6-o-anisyl-(η⁵-4,5-tetrahydropentalene)]dichlorozirconium
[4-(η⁵-fluorenyl)-2-ethyl-4-methyl-6-o-anisyl-(η⁵-4,5-tetrahydropentalene)]dichlorozirconium
[4-(η⁵-fluorenyl)-2-isopropyl-4-methyl-6-o-anisyl-(η⁵-4,5-tetrahydropentalene)]dichlorozirconium
[4-(η⁵-fluorenyl)-2-tert-butyl-4-methyl-6-o-anisyl-(η⁵-4,5-tetrahydropentalene)]dichlorozirconium
[4-(η⁵-fluorenyl)-2-benzyl-4-methyl-6-o-anisyl-(η⁵-4,5-tetrahydropentalene)]dichlorozirconium
[4-(η⁵-fluorenyl)-2-trimethylsilyl-4-methyl-6-o-anisyl-(η⁵-4,5-tetrahydropentalene)]dichlorozirconium
[4-(η⁵-fluorenyl)-2-methyl-4,6-diphenyl-(η⁵-4,5-tetrahydropentalene)]dichlorozirconium
[4-(η⁵-fluorenyl)-2-ethyl-4,6-diphenyl-(η⁵-4,5-tetrahydropentalene)]dichlorozirconium
[4-(η⁵-fluorenyl)-2-isopropyl-4,6-diphenyl-(η⁵-4,5-tetrahydropentalene)]dichlorozirconium
[4-(η⁵-fluorenyl)-2-tert-butyl-4,6-diphenyl-(η⁵-4,5-tetrahydropentalene)]dichlorozirconium
[4-(η⁵-fluorenyl)-2-benzyl-4,6-diphenyl-(η⁵-4,5-tetrahydropentalene)]dichlorozirconium
[4-(η⁵-fluorenyl)-2-trimethylsilyl-4,6-diphenyl-(η⁵-4,5-tetrahydropentalene)]dichlorozirconium
[4-(η⁵-fluorenyl)-2,4-dimethyl-6-p-tolyl-(η⁵-4,5-tetrahydropentalene)]dichlorozirconium
[4-(η⁵-fluorenyl)-2,4-ethyl-4-methyl-6-p-tolyl-(η⁵-4,5-tetrahydropentalene)]dichlorozirconium
[4-(η⁵-fluorenyl)-2-isopropyl-4-methyl-6-p-tolyl-(η⁵-4,5-tetrahydropentalene)]dichlorozirconium
[4-(η⁵-fluorenyl)-2-tert-butyl-4-methyl-6-p-tolyl-(η⁵-4,5-tetrahydropentalene)]dichlorozirconium
[4-(η⁵-fluorenyl)-2-benzyl-4-methyl-6-p-tolyl-(η⁵-4,5-tetrahydropentalene)]dichlorozirconium
[4-(η⁵-fluorenyl)-2-trimethylsilyl-4-methyl-6-p-tolyl-(η⁵-4,5-tetrahydropentalene)]dichlorozirconium
[4-(η⁵-fluorenyl)-2,4-dimethyl-6-naphthyl-(η⁵-4,5-tetrahydropentalene)]dichlorozirconium
[4-(η⁵-fluorenyl)-2-ethyl-4-methyl-6-naphthyl-(η⁵-4,5-tetrahydropentalene)]dichlorozirconium
[4-(η⁵-fluorenyl)-2-isopropyl-4-methyl-6-naphthyl-(η⁵-4,5-tetrahydropentalene)]dichlorozirconium
[4-(η⁵-fluorenyl)-2-tert-butyl-4-methyl-6-naphthyl-(η⁵-4,5-tetrahydropentalene)]dichlorozirconium
[4-(η⁵-fluorenyl)-2-benzyl-4-methyl-6-naphthyl-(η⁵-4,5-tetrahydropentalene)]dichlorozirconium
[4-(η⁵-fluorenyl)-2-trimethylsilyl-4-methyl-6-naphthyl-(η⁵-4,5-tetrahydropentalene)]dichlorozirconium
[4-(η⁵-fluorenyl)-2,4-dimethyl-6-phenyl-(η⁵-4,5-tetrahydropentalene)]dichlorotitanium
[4-(η⁵-fluorenyl)-2,4-dimethyl-6-phenyl-(η⁵-4,5-tetrahydropentalene)]dichlorohafnium
[4-(η⁵-fluorenyl)-2,4-dimethyl-6-phenyl-(η⁵-5-tetrahydropentalene)]bis(diethylamino)zirconium
[4-(η⁵-fluorenyl)-2,4-dimethyl-6-phenyl-(η⁵-4,5-tetrahydropentalene)]bis(dimethylamino)zirconium The naming of the abovementioned compounds of the invention is illustrated by means of the compound [4-(η⁵-3'-isopropylcyclopentadienyl)-4,6,6-trimethyl-(η⁵-4,5-tetrahydropentalene)]dichlorozirconium.

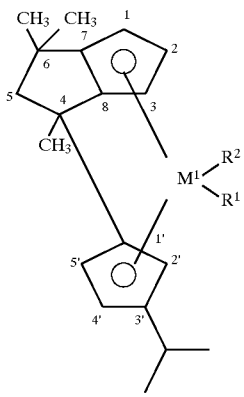

The preparation of the metallocenes of the invention is illustrated by the following reaction scheme for metallocenes of the formula VI. In this scheme, M⁴ is a metal of main group Ia, IIa or IIIa of the Periodic Table of the Elements, Hal is a halogen atom, the radicals R³–R¹¹, R¹³ and R¹⁴ are as defined for formula I and R¹² is hydrogen.

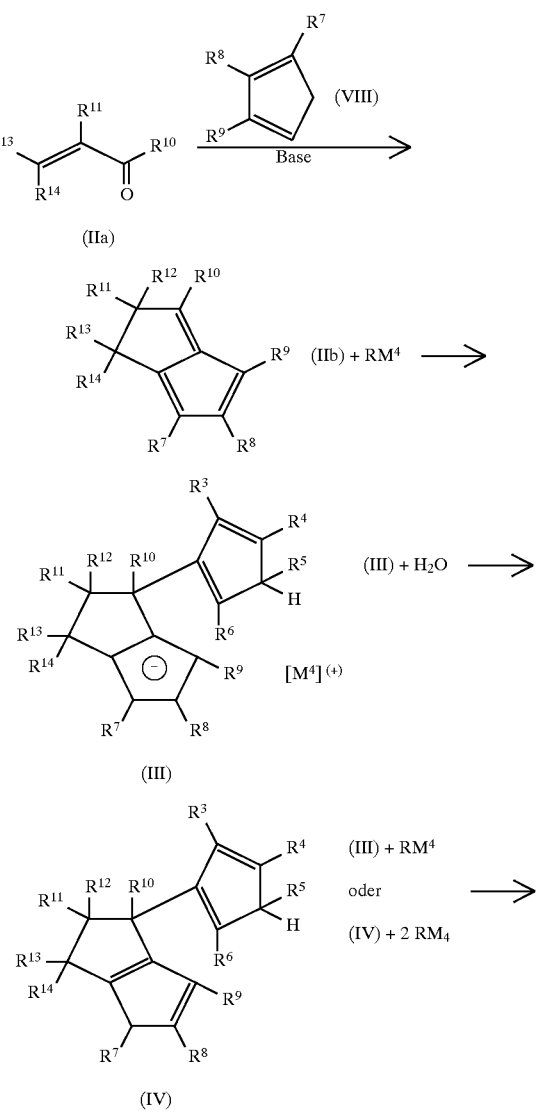

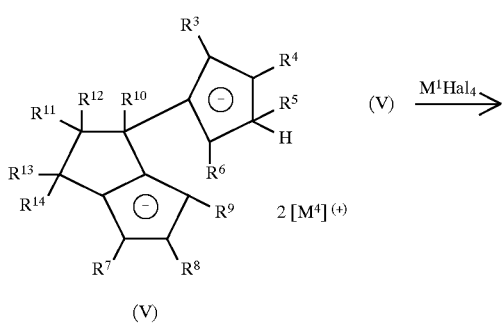

(V)

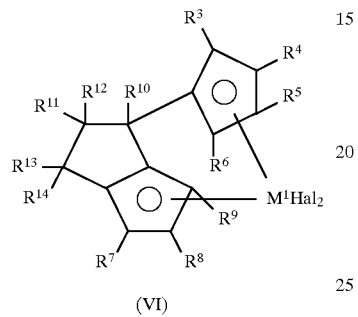

(VI)

The compounds of the formula IIb can be prepared from α,β-unsaturated ketones (Chem. Ber. 123, 549 (1990), J. Org. Chem. 54, 4981 (1989)) by methods known from the literature.

The conversion of the compound of the formula IIb into the ligand system III is carried out by reaction with a compound $RM^4$ which can be an organometallic compound (e.g. cyclopentadienyllithium, indenyllithium, fluorenyllithium or a Grignard reagent (e.g. cyclopentadienylMgHal, indenylMgHal, fluorenylMgHal).

The salts of the formula III can be converted directly into the corresponding dianionic compounds of the formula V by deprotonation using, for example, butyllithium. The hydrolysis of compound III leads to formation of the bis-cyclopentadienyl compound IV which is formed as a mixture of structural isomers and can be purified by chromatography. Double deprotonation of IV using, for example, butyllithium forms the dianionic compound of the formula V which is reacted with $M^1Hal_4$ to give the metallocene of the formula VI.

Metallocenes of the formula VI can be reacted with organometallic compounds such as Grignard reagents or hydrocarbon-lithium reagents to give metallocenes of the formula I in which $R^1$ and $R^2$ are not halogen. The reaction to form the bridged metallocenes of the formula VI as well as the isolation of the desired complexes is known in principle. For this purpose, the dianion of the formula V is reacted in an inert solvent with the appropriate metal halide such as zirconium tetrachloride. The metallocenes of the formula VI can also be simplified directly from the difulvenes of the formula II without isolation of the intermediates.

Suitable solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

A further possible way of preparing the metallocene compounds of the invention is reacting the ligand precursor VII with the cyclopentadiene VIII, each of which can be prepared by methods known from the literature. The compounds IX can, using a method known from the literature, be cyclized thermally to give the ligand precursors X (Chem. Ber. 120, 1611 (1987)). The conversion of X into XI is carried out using an organometallic compound (e.g. cyclopentadienyllithium, indenyllithium, fluorenyllithium) or Grignard reagents.

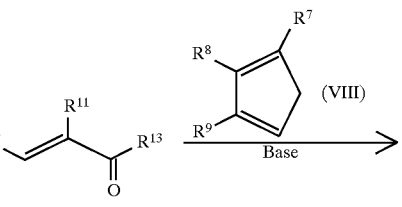

(VII)        (VIII)

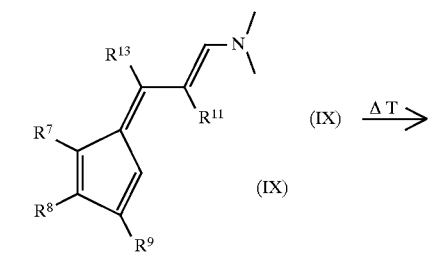

(IX)

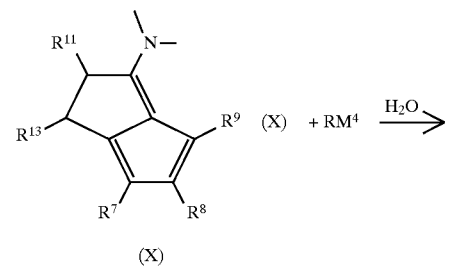

(X)

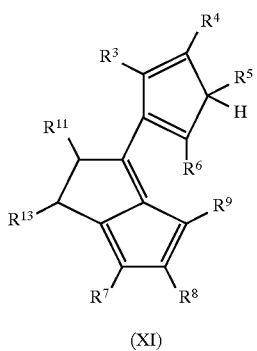

(XI)

The dianionic compound of the formula Va can be obtained directly by reaction of X with an organometallic reagent (e.g. phenyllithium, methyllithium, n-butyllithium or Grignard reagents). The hydrolysis of Va with water gives the ligand precursor IV.

The reaction to form the bridged metallocenes of the formula VIa as well as the isolation of the desired complexes is known in principle. For this purpose, the dianion of the formula Va is reacted in an inert solvent with the appropriate metal halide such as zirconium tetrachloride. The metallocenes of the formula VIa can also be synthesized directly from the fulvenes of the structure X without isolation of the intermediates.

Suitable solvents are aliphatic or aromatic solvents such as hexane or toluene, ether solvents such as tetrahydrofuran and diethyl ether or halogenated hydrocarbons such as methylene chloride or halogenated aromatic hydrocarbons such as o-dichlorobenzene.

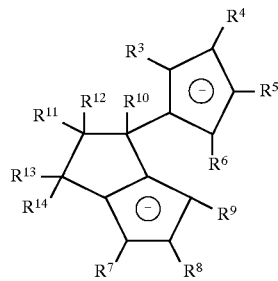

(Va)

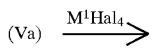

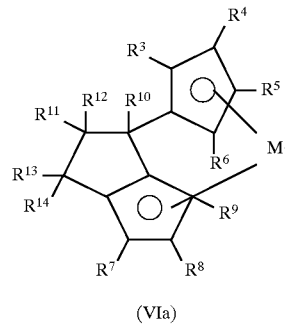

(VIa)

Biscyclopentadienyl compounds of the formula IV in which at least one of the radicals $R^3$ to $R^6$ and at least one of the radicals $R^7$ to $R^9$ are hydrogen and at least one of the radicals $R^3$ to $R^9$ is not hydrogen can be converted into the fulvenes of the formulae IVb and IVc by methods known from the literature. This is illustrated by the following reaction scheme, where $R^{16}$, $R^{17}$, $R^{19}$ and $R^{20}$ are identical or different and are as defined for $R^{10}$.

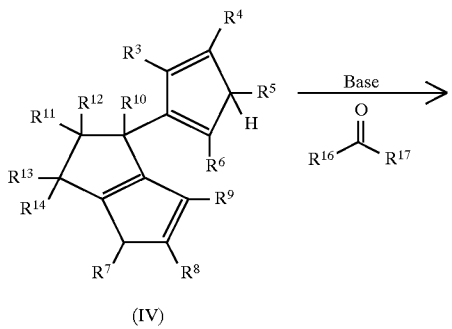

(IV)

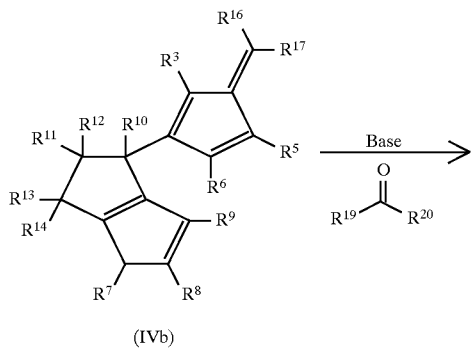

(IVb)

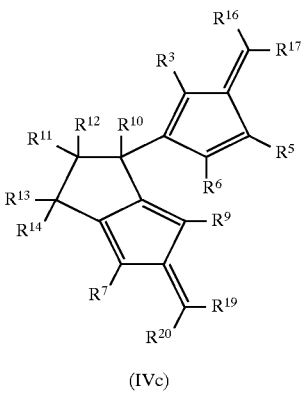

(IVc)

Reaction of the fulvene IVb with organometallic compounds of the formula $R^{18}M^5$ (where $R^{16}$, $R^{17}$ $R^{18}$ $R^{19}$ and $R^{20}$ are identical or different and are as defined for $R^{10}$; $M^5$ is defined as for $M^4$) leads to formation of the monoanionic compound III. The use of two equivalents of $R^{18}M^5$ leads directly to the formation of the dianionic compound Vb.

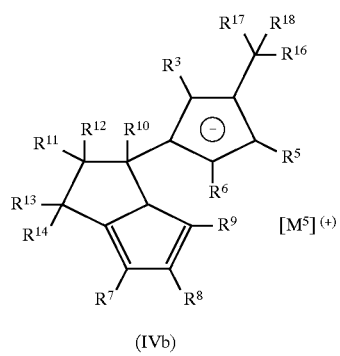

(IVb)

-continued

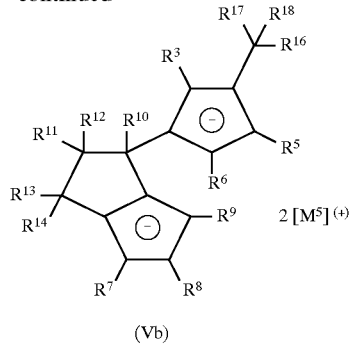

(Vb)

The reaction of the fulvene IVc leads, analogously to the reaction of IVa, to formation of the dianionic compound Vc.

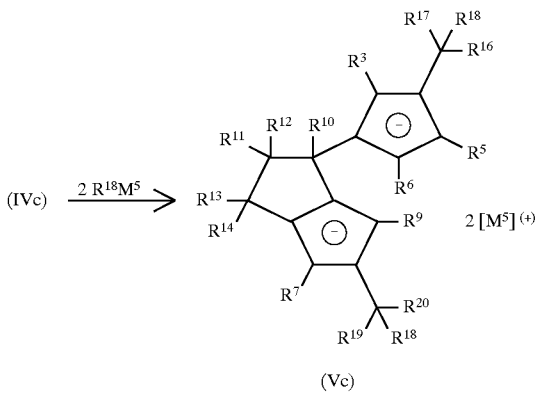

(Vc)

The biscyclopentadienyl anions of the formula V can be reacted with compounds $R^{21}_pM^6X$, where $M^6$ is an element of main groups III–V, X is a leaving group such as halogen, tosylate, triflate, $R^{21}$ is as defined for $R^{10}$, and p is an integer from 1 to 5.

This is illustrated by the following reaction scheme:

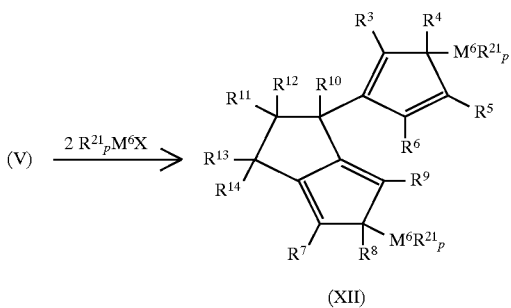

(XII)

Compounds of the formula XII in which at least one of the radicals $R^3$ to $R^6$ and at least one of the radicals $R^7$ to $R^9$ are hydrogen can be converted into the metallocenes of the invention.

$R^{12}$ in the compounds of the formulae IIb, III, IV, V, VI, X, XI, Va, VIa, IVb, IVc, Vb, Vc and XII is hydrogen. $R^{14}$ in the compounds of the formulae X, XI, Va and VIa is hydrogen. The salts of the formula IIIb can be converted directly into the corresponding dianionic compounds of the formula Va by deprotonation using, for example, butyl-lithium. The conversion into the metallocenes of the formula I is carried out analogously to the reaction of V to give VI.

The metallocenes of the invention are highly active catalyst components for olefin polymerization. Depending on the substitution pattern of the ligands, the metallocenes can be formed as a mixture of isomers. The metallocenes are preferably used in isomerically pure form. The use of the racemate is sufficient in most cases.

However, it is also possible to use the pure enantiomer in the (+) or (−) form. Use of a pure enantiomer enables the preparation of an optically active polymer. However, the configurational isomers of the metallocenes should be separated since the polymerization-active center (the metal atom) in these compounds produces a polymer having different properties. For certain applications, for example flexible moldings, this can be very desirable.

The present invention also provides a process for preparing a polyolefin by polymerization of at least one olefin in the presence of a catalyst which comprises at least one cocatalyst and at least one stereorigid metallocene compound of the formula I. For the purposes of the present invention, the term polymerization means either homopolymerization or copolymerization.

In the process of the invention, preference is given to polymerizing one or more olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, and $R^a$ and $R^b$ together with the atoms connecting them may form one or more rings. Examples of such olefins are 1-olefins having from 2 to 40, preferably 2–10, carbon atoms, e.g. ethylene, propylene, 1-butene, 1-pentene, 1-hexene, 4-methyl-1-pentene or 1-octene, styrene, dienes such as 1,3-butadiene, isoprene, 1,4-hexadiene or cyclic olefins. Preference is given, in the process of the invention, to homopolymerizing ethylene or propylene or copolymerizing ethylene with one or more cyclic olefins such as norbornene and/or one or more acyclic 1-olefins having from 3 to 20 carbon atoms, e.g. propylene, and/or one or more dienes having from 4 to 20 carbon atoms, e.g. 1,3-butadiene or 1,4-hexadiene. Examples of such copolymers are ethylene-norbornene copolymers, ethylene-propylene copolymers and ethylene-propylene-1,4-hexadiene copolymers.

The polymerization is preferably carried out at a temperature of from −60° to 250° C., particularly preferably from 50° to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. Preferred embodiments are gas-phase and solution polymerization.

The catalyst used in the process of the invention preferably comprises one metallocene compound. It is also possible to use mixtures of two or more metallocene compounds, e.g. for preparing polyolefins having a broad or multimodal molecular weight distribution.

In principle, a suitable cocatalyst in the process of the invention is any compound which, owing to its Lewis acidity, can convert the neutral metallocene into a cation and stabilize the latter ("labile coordination"). Furthermore, the cocatalyst or the anion formed therefrom should undergo no further reactions with the metallocenium cation formed (EP 427 697). The cocatalyst used is preferably an aluminum compound and/or a boron compound.

The boron compound preferably has the formula $R^{22}_xNH_{4-x}BR^{23}_4$, $R^{22}_xPH_{4-x}BR^{23}_4$, $R^{22}_3CBR^{23}_4$ or $BR^{23}_3$, where x is a number from 1 to 4, preferably 3, the radicals $R^{22}$ are identical or different, preferably identical, and are $C_1$–$C_{10}$-alkyl or $C_6$–$C_{18}$-aryl or two radicals $R^{22}$ together with the atoms connecting them form a ring, and the radicals $R^{23}$ are identical or different, preferably identical, and are $C_6$–$C_{18}$-aryl which may be substituted by alkyl, haloalkyl or fluorine. In particular, $R^{22}$ is ethyl, propyl, butyl or phenyl and $R^{23}$ is phenyl, pentafluorophenyl, 3,5-bis (trifluoromethyl)phenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula XIIIa for the linear type and/or the formula XIIIb for the cyclic type,

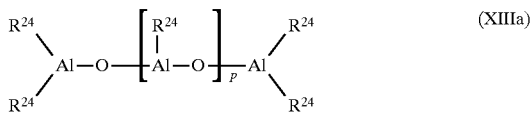

where, in the formulae XIIIa and XIIIb, the radicals $R^{24}$ are identical or different and are each hydrogen or a $C_1$–$C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^{24}$ are preferably identical and are hydrogen, methyl, isobutyl, phenyl or benzyl, particularly perferably methyl.

If the radicals $R^{24}$ are different, they are preferably methyl and hydrogen or alternatively methyl and isobutyl, where hydrogen or isobutyl are preferably present in a proportion by number of from 0.01 to 40% (of the radicals $R^{24}$).

The methods of preparing the aluminoxanes are known. The exact spatial structure of the aluminoxanes is not known (J. Am. Chem. Soc. (1993) 115, 4971). For example, it is conceivable that chains and rings are joined to form larger two-dimensional or three-dimensional structures.

Regardless of the method of preparation, all aluminoxane solutions have in common a varying content of unreacted aluminum starting compound which is present in free form or as adduct.

Before use in the polymerization reaction, the metallocene compound can be preactivated using a cocatalyst, in particular an aluminoxane. This significantly increases the polymerization activity. The preactivation of the metallocene compound is preferably carried out in solution. Here, the metallocene compound is preferably dissolved in a solution of the aluminoxane in an inert hydrocarbon. Suitable inert hydrocarbons are aliphatic or aromatic hydrocarbon. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^{-4}$ to 1 mol per mole of aluminoxane. The preactivation time is from 5 minutes to 60 hours, preferably from 5 to 60 minutes. The preactivation is carried out at a temperature of from −78° to 100° C., preferably from 0° to 80° C.

The metallocene compound is preferably employed in a concentration, based on the transition metal, of from $10^{-3}$ to $10^{-8}$ mol, preferably from $10^{-4}$ to $10^{-7}$ mol of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the metallocene compound. However, higher concentrations are also possible in principle.

The aluminoxane can be prepared in various ways by known methods. One method is, for example, reacting an aluminum-hydrocarbon compound and/or a hydridoaluminum-hydrocarbon compound with water (gaseous, solid, liquid or bound, for example as water of crystallization) in an inert solvent (such as toluene). To prepare an aluminoxane having different radicals $R^{24}$, for example, two different trialkylaluminums corresponding to the desired composition are reacted with water.

To remove catalyst poisons present in the olefin, it is advantageous to carry out a purification using an aluminum compound, preferably an aluminum alkyl such as trimethylaluminum or triethylaluminum. This purification can be carried out either in the polymerization system itself or the olefin is brought into contact with the aluminum compound and subsequently separated off again before it is added to the polymerization system.

As molecular weight regulator and/or to increase the catalyst activity, hydrogen can be added in the process of the invention. This enables low molecular weight polyolefins such as waxes to be obtained.

In the process of the invention, the metallocene compound is preferably reacted with the cocatalyst outside the polymerization reactor in a separate step using a suitable solvent. It can be applied to a support during this step.

A prepolymerization using the metallocene compound can be carried out in the process of the invention. For the prepolymerization, preference is given to using the (or one of the) olefin(s) used in the polymerization.

The catalyst used in the process of the invention can be supported. Application to a support allows, for example, the particle morphology of the polyolefin produced to be controlled. Here, the metallocene compound can be reacted first with the support and subsequently with the cocatalyst. The cocatalyst can also be applied to the support first and subsequently reacted with the metallocene compound. It is also possible to apply the reaction product of metallocene compound and cocatalyst to the support. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can be carried out, for example, as described in EP 567 952.

The cocatalyst, e.g. aluminoxane, is preferably applied to a support such as silica gels, aluminum oxides, solid aluminoxane, other inorganic support materials or a polyolefin powder in finely divided form and then reacted with the metallocene.

Inorganic supports which can be used are oxides which are produced flame-pyrolytically by combustion of element halides in a hydrogen/oxygen flame or can be prepared as silica gels having particular size distributions and particle shapes.

The preparation of the supported cocatalyst can be carried out, for example, as described in EP 578 838 in the following manner in a stainless steel reactor of explosionproof design with a pumped circulation system having a pressure rating of 60 bar, with inert gas supply, temperature control by means of jacket cooling and a second cooling circuit via a heat exchanger on the pumped circulation system. The pumped circulation system draws in the reactor contents via a connection in the bottom of the reactor by means of a pump and pushes it into a mixer and through a riser line via a heat exchanger back into the reactor. The mixer is configured such that the inlet has a constricted pipe cross section where the flow velocity is increased and into whose turbulence zone there is introduced, axially and in a direction opposite to the flow, a thin feed line through which, pulsed, in each case a define amount of water under 40 bar of argon can be fed in. The reaction is controlled via a sampler on the pumped circuit.

However, other reactors are also suitable in principle.

The above-described reactor having a volume of 16 dm$^3$ is charged with 5 dm$^3$ of decane under inert conditions. 0.5 dm$^3$ (=5.2 mol) of trimethylaluminum is added at 25° C. 250 g of silica gel SD 3216-30 (Grace AG) which have been dried beforehand at 120° C. in an argon-fluidized bed are then introduced into the reactor via a solids funnel and are distributed homogeneously by means of the stirrer and the pumped circulation system. A total amount of 76.5 g of water is added to the reactor in portions of 0.1 cm$^3$ every 15 seconds over a period of 3.25 hours. The pressure, resulting from the argon and the gases evolved, is kept constant at 10 bar by means of a pressure regulation valve. After all the water has been introduced, the pumped circulation system is switched off and stirring is continued for 5 hours at 25° C.

The supported cocatalyst prepared in this way is used as a 10% strength suspension in n-decane. The aluminum content is 1.06 mmol of Al per cm$^3$ of suspension. The isolated solid contains 31% by weight of aluminum, the suspension medium contains 0.1% by weight of aluminum.

Further possible ways of preparing a supported catalyst are described in EP 578 838.

The metallocene of the invention is then applied to the supported cocatalyst by stirring the dissolved metallocene with the supported cocatalyst. The solvent is removed and replaced by a hydrocarbon in which both cocatalyst and metallocene are insoluble.

The reaction to form the supported catalyst system is carried out at a temperature of from −20° to +120° C., preferably from 0° to 100° C., particularly preferably at from 15° to 40° C. The metallocene is reacted with the supported cocatalyst by combining the cocatalyst as a 1–40% by weight, preferably 5–20% by weight, suspension in an aliphatic, inert suspension medium such as n-decane, hexane, heptane or diesel oil with a solution of the metallocene in an inert solvent such as toluene, hexane, heptane or dichloromethane or with the finely milled solid metallocene. Conversely, a solution of the metallocene can also be reacted with the solid cocatalyst.

The reaction is carried out by intensive mixing, for example by stirring at a molar Al/M$^1$ ratio of from 100/1 to 10,000/1, preferably from 100/1 to 3000/1, and a reaction time of from 5 to 120 minutes, preferably from 10 to 60 minutes, particularly preferably from 10 to 30 minutes, under inert conditions. During the course of the reaction for preparing the supported catalyst system, particularly when using the metallocenes of the invention having absorption maxima in the visible range, changes occur in the color of the reaction mixture and these can be used to follow the progress of the reaction.

After the reaction time has elapsed, the supernatant solution is separated off, for example by filtration or decantation. The remaining solid is washed from 1 to 5 times with an inert suspension medium such as toluene, n-decane, hexane, diesel oil or dichloromethane to remove soluble constituents in the catalyst formed, in particular to remove unreacted and therefore insoluble metallocene.

The supported catalyst system thus prepared can be resuspended as a vacuum-dried solid or while still moist with solvent and metered as a suspension in one of the abovementioned inert suspension media into the polymerization system.

If the polymerization is carried out as a suspension or solution polymerization, use is made of an inert solvent customary for the Ziegler low-pressure process. For example, the polymerization is carried out in an aliphatic or cycloaliphatic hydrocarbon, for example propane, butane, hexane, heptane, isooctane, cyclohexane or methylcyclohexane. It is also possible to use a petroleum or hydrogenated diesel oil fraction. Toluene can also be used. Preference is given to carrying out the polymerization in the liquid monomer.

Before addition of the catalyst in particular the supported catalyst system (comprising the metallocene of the invention and a supported cocatalyst), another aluminum alkyl compound such as trimethylaluminum, triethylaluminum, triisobutylaluminum, trioctylaluminum or isoprenylaluminum can be additionally introduced into the reactor for making the polymerization system inert (for example for removing catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a small Al/M$^1$ molar ratio to be employed in the synthesis of a supported catalyst system.

If inert solvents are used, the monomers are metered in in gaseous or liquid form.

The polymerization time can be any desired, since the catalyst system to be used in the process of the invention displays only a slight time-dependent decrease in the polymerization activity.

The specific stereorigid metallocene compounds described in the present invention are suitable for preparing polyolefins, in particular those having a reduced crystallinity, increased impact toughness, increased transparency, high flowability at processing temperature and also a reduced melting point.

Major applications of such polyolefins are plasticizer and lubricant formulations, melt adhesive applications, coatings, seals, insulation, filling compounds or sound insulation materials.

Use of hydrogen or increasing the polymerization temperature also makes it possible to obtain polyolefins having a low molar mass, for example waxes, whose hardness or melting point can be varied by means of the comonomer content.

Conversely, selection of the polymerization conditions also makes it possible to prepare high molecular weight polyolefins which are suitable as thermoplastic materials. These are suitable, in particular, for producing shaped bodies such as films, sheets or large hollow bodies (e.g. pipes).

Selection of the polymerization process and the type(s) and amount(s) of comonomer(s) allows the preparation of olefin copolymers having elastomeric properties, for example ethylene-propylene-1,4-hexadiene terpolymers.

The following examples serve to illustrate the invention.

Preparation and handling of organometallic compounds were carried out with exclusion of air and moisture under argon (Schlenk technique). All solvents required were made absolute before use by boiling for a number of hours over a suitable desiccant and subsequent distillation under argon.

The α,β-unsaturated ketones and fulvenes used as starting compounds were prepared by methods known from the literature (Synlett 771 (1991); J. Chem. Soc., Commun. 1694 (1986); Chem. Ber. 116, 119 (1983); Tetrahedron Lett. 23; 1447 (1982)); cyclopentadiene and methylcyclopentadiene were obtained by cracking of the dimers and were stored at −35° C.

The compounds prepared were analyzed by $^1$H-NMR.

1. 4-Cyclopentadienyl-4,6,6-trimethyl-4,5-tetrahydropentalene

The preparation was carried out by a method known from the literature (*Makromol. Chem,* 183 (1982), 359) by reacting 6,6-dimethylfulvene with sodium cyclopentadienide.

2. [4-($\eta^5$-Cyclopentadienyl)-4,6,6-trimethyl-($\eta^5$-4,5-tetrahydropentalene)]dichlorozirconium 59.1 ml (94.6 mmol) of a 1,6 molar methyllithium solution in hexane are added dropwise to a solution of 10 g (47.2 mmol) of 4-cyclopentadienyl-4,6,6-trimethyl-4,5-tetrahydropentalene in 50 ml of toluene. The solution is stirred further for 3 hours. The resulting suspension is cooled to −78° C. and 11 g (47.2 mmol) of zirconium tetrachloride are subsequently added a little at a time. The suspension is stirred for 24 hours and subsequently filtered through a G3 frit. The residue is extracted with 100 ml of toluene and the combined toluene filtrates are freed of solvent under reduced pressure. This gives 7.4 g (42%) of [4-($\eta^5$-cyclopentadienyl)-4,6,6-trimethyl-($\eta^5$-4,5-tetrahydropentalene)]dichlorozirconium in the form of a yellow powder.

$^1$H-NMR (200 MHz, CDCl$_3$): 7.2–5.9 (m, 7H, H-C(2'), H-C(3'), H-C(4'), H-C(5'), H-C(1), H-C(2), H-C(3)), 3.3 (d, 14, 1H, H-C(5)), 2.9 (d, 14, 1H, H-C(5)), 2.3 (s, 3H, CH$_3$), 1.8 (s, 3H, CH$_3$), 1.75 (s, 3H, CH$_3$).

3. 4-(3'-Isopropylidenecyclopentadienyl)-4,6,6,-trimethyl-4,5-tetrahydropentalene 4.98 g (70 mmol) of pyrrolidine are added dropwise at 0° C. to a solution of 15 g (35 mmol) of 4-cyclopentadienyl-4,6,6-trimethyl-4,5-tetrahydropentalene and 2.64 g (45.5 mmol) of acetone in 150 ml of methanol. The reaction solution is stirred further for 24 hours at 0° C. and the reaction is stopped by addition of 4.2 g (70 mmol) of glacial acetic acid. The mixture is subsequently extracted 3 times with 70 ml each time of pentane and the combined extracts are washed with sodium chloride solution and dried over magnesium sulfate. Removing the solvent under reduced pressure gives 9.4 g (81 %) of 4-(3'-isopropylidene-cyclopentadienyl)-4,6,6-trimethyl4,5-tetrahydropentalene.

4. 4-(3'-Isopropylcyclopentadienyl)-4,6,6-trimethyl-4,5-tetrahydropentalene

A solution of 10 g (39.4 mmol) of 4-(3'-isopropylidene-cyclopentadienyl)-4,6,6-trimethyl-4,5-tetrahydropentalene in 30 ml of diethyl ether is added dropwise at room temperature to a suspension of 4.5 g (118.5 mmol) of lithium aluminum hydride in 120 ml of diethyl ether. The reaction mixture is stirred for one hour at room temperature and subsequently heated under reflux for a further 3 hours. After the reaction is complete, the mixture is cooled to 0° C. and hydrolyzed with iced water. The precipitated form is filtered off and extracted 3 times with 20 ml each time of diethyl ether. The combined ether extracts are dried over magnesium sulfate and the solvent is removed under reduced pressure. This gives 9.5 g (94%) of 4-(3'-isopropylcyclopentadienyl)-4,6,6-trimethyl-4,5-tetrahydropentalene.

5. [4-($\eta^5$-3'-Isopropylcyclopentadienyl)-4,6,6-trimethyl-($\eta^5$-4,5-tetrahydropentalene)]dichlorozirconium 39 ml (62.4 mmol) of a 1.6 molar methyllithium solution in hexane are added dropwise to a solution of 8 g (31.2 mmol) of 4-(3'-isopropyl-cyclopentadienyl)-4,6,6-trimethyl-4,5 -tetrahydropentalene in 40 ml of toluene. The solution is stirred further for 3 hours. The resulting suspension is cooled to −78° C. and 7.3 g (31.3 mmol) of zirconium tetrachloride are subsequently added a little at a time. The suspension is stirred for 24 hours and subsequently filtered through a G3 frit. The residue is extracted with 80 ml of toluene and the combined toluene filtrates are freed of solvent under reduced pressure. This gives 5.6 g (45%) of [4-($\eta^5$-3'-isopropylcyclopentadienyl)-4,6,6-trimethyl-($\eta^5$-4,5-tetrahydropentalene)]dichlorozirconium in the form of a yellow powder.

$^1$H-NMR (200 MHz, CDCl$_3$): 7.4–5.9 (m, 7H, H-C(2'), H-C(4'), H-C(5'), H-C(1), H-C(2), H-C(3)), 3.3 (d, 14, 1H, H-C(5)), 2.95 (d, 14, 1H, H-C(5)), 2.2 (s, 3H, CH$_3$), 2.05 (m, 1H, Me$_2$CH), 1.85 (s, 3H, CH$_3$), 1.75 (s, 3H, CH$_3$), 1.3 (d, 8, 6H, Ch$_3$)$_2$C).

6. 4-(3'-Trimethylsilylcyclopentadienyl)-4,6,6-trimethyl-4,5-tetrahydropentalene 16 ml (35 mmol) of a 2.5 molar solution of n-butyllithium in hexane are added at 0° C. to a solution of 8.5 g (40 mmol) of 4-cyclopentadienyl-4,6,6-trimethyl-4,5-tetrahydropentalene in 100 ml of THF. The reaction solution is stirred further for 2 hours at 0° C. and 6.3 ml (50 mmol) of trimethylsilyl chloride are then added. After 2 hours, volatile constituents are distilled off in an oil pump vacuum and the residue is subsequently extracted with 70 ml of pentane and filtered. The filtrate is dried under reduced pressure. This gives 10.8 g (38 mmol) of 4-(3'-trimethylsilyl-cyclopentadienyl)-4,6,6-trimethyl-4,5-tetrahydro-pentalene in the form of a yellowish oil.

7. [4-($\eta^5$-3'-Trimethylsilylcyclopentadienyl)-4,6,6-trimethyl-($\eta^5$-4,5-tetrahydropentalene)]dichlorozirconium 30.5 ml (76 mmol) of a 2.5 molar n-butyllithium solution in hexane are added to a solution of 10.8 g (38 mmol) of 4-(3'-trimethylsilyl-cyclopentadienyl)-4,6,6-trimethyl-4,5-tetrahydropentalene in 100 ml of toluene. The solution is stirred for 3 hours at 22° C. and is then cooled to −78° C. 8.85 g (38 mmol) of zirconium tetrachloride are subsequently added a little at a time. The suspension is stirred for 24 hours at room temperature and subsequently filtered through a G3 frit. The residue is extracted with 100 ml of toluene and the combined toluene filtrates are freed of solvent under reduced pressure. This gives 6.3 g (38%) of [4-($\eta^5$-3'-trimethylsilylcyclopentadienyl)-4,6,6-trimethyl-($\eta^5$-4,5-tetrahydropentalene)]dichlorozirconium as an isomer mixture in the form of a yellowish powder.

$^1$H-NMR (200 MHz, CDCl$_3$): 6.9–5.3 (m, 6H, H-C(2'), H-C(4'), H-C(5'), H-C(1), H-C(3)), 2.85 (m, 14, 1H, H-C(5)), 2.45 (m, 14, 1H, H-C(5)), 2.3 (m, 3H, CH$_3$), 1.9 (m, 3H, CH$_3$), 1.35 (m, 6H, CH$_3$), 0.23 (s, CH$_3$—Si), 0.22 (s, CH$_3$—Si).

Polymerization example A 4.3 mg [4-($\eta^5$-cyclopentadienyl)-4,6,6-trimethyl($\eta^5$-4,5-tetrahydropentalene)]dichlorozirconium (0.0120 mmol of Zr) were dissolved under argon while stirring in 1.5 ml of toluene in a Schlenk tube. To activate the catalyst, 3.5 ml of 30% strength MAO (16.59 mmol of Al; Zr:Al =1:3530) from Witco were then added and the resulting solution was added to 750 ml of Exxsol 100/120.

The catalyst solution was transferred to an autoclave in which polymerization was carried out for one hour at a temperature of 70° C., a stirrer speed of 750 rpm and an ethylene partial pressure of 4 bar. After the end of the reaction time, the ethene was released from the reactor and the polymerization mixture was stirred with a little ethanol. It was then drained from the reactor and stirred overnight with a 10% strength ethanolic hydrochloric acid solution. It was subsequently washed with saturated NaHCO$_3$ solution and twice with about 100 cm$^3$ of water. The polymer was filtered off and dried to constant weight at 60° C. under reduced pressure. 34 g of polyethylene were obtained.

Polymerization example B

The polymerization and work-up were carried out as described in polymerization example A. However, 3.4 g of

[4-(3'-isopropyl-$\eta^5$-cyclopentadienyl)-4,6,6-trimethyl-($\eta^5$-4,5-tetrahydropentalene)]-dichlorozirconium were used as metallocene. 71 g of polyethylene were obtained.

We claim:

1. A stereorigid metallocene compound of the formula I

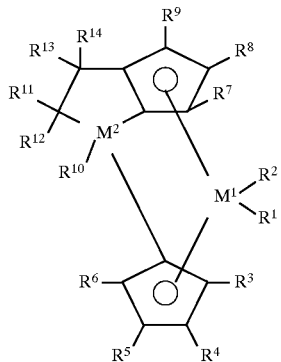

where $M^1$ is a metal of group IIIb, IVb, Vb or VIb of the Periodic Table, $M^2$ is carbon, silicon or germanium, $R^1$ and $R^2$ are identical or different and are each a hydrogen atom, a $C_1$–$C_{40}$-group, an OH group, a halogen atom or $NR^{15}_2$, where $R^{15}$ is a halogen atom, a $C_1$–$C_{10}$-alkyl group or a $C_6$–$C_{10}$-aryl group, or $R^1$ and $R^2$ together with the atoms connecting them form a ring system, $R^3$, $R^4$, $R^5$, $R^6$, $R^7$, $R^8$ and $R^9$ are identical or different and are each a hydrogen atom, a halogen atom, a $C_1$–$C_{40}$-group, which is optionally halogenated an —$SiR^{15}_3$, —$NR^{15}_2$, —$SiOR^{15}_3$, —$SiSR^{15}_3$ or —$PR^{15}_2$ radical, where $R^{15}$ are identical or different and are each a halogen atom, a $C_1$–$C_{10}$-alkyl group or a $C_6$–$C_{10}$-aryl group or form a ring system, or two or more adjacent radicals $R^3$, $R^4$, $R^5$, $R^6$, $R^7$, $R^8$ and $R^9$ together with the atoms connecting them form a ring system $R^{10}$, $R^{13}$ and $R^{14}$ are identical or different, and are each a $C_1$–$C_{20}$-alkyl group, $R^{11}$ and $R^{12}$ are identical or different and are each a hydrogen atom, a $C_1$–$C_{40}$-group, each of which may bear radicals such as a halogen atom, —$NR^{15}_3$, —$SR^{15}_2$, —$SiR^{15}_3$ or —$OSiR^{15}_3$, where $R^{15}$ is a halogen atom, a $C_1$–$C_{10}$-alkyl group or a $C_1$–$C_{10}$-aryl group, and the ligand system of the compound of the formula I is different from 4-($\eta^5$-3'-alkylcyclopentadienyl)-4,6,6-trimethyl-($\eta^5$-2-alkyl-4,5-tetrahydropentalene).

2. The stereorigid metallocene compound of the formula I as claimed in claim 1, wherein $M^1$ is a metal of group IVb of the Periodic Table of the Elements, $R^1$ and $R^2$ are identical and are each a $C_1$–$C_4$-alkyl group or a halogen atom, $R^3$, $R^4$, $R^5$, $R^6$, $R^7$, $R^8$ and $R^9$ are identical or different and are each a hydrogen atom, a $C_1$–$C_{10}$-alkyl group or a $C_6$–$C_{24}$-aryl group, or two or more adjacent radicals $R^3$, $R^4$, $R^5$, $R^6$, $R^7$, $R^8$ and $R^9$ together with the atoms connecting them form an aromatic or aliphatic ring system having from 4 to 20 carbon atoms, $R^{10}$, $R^{13}$ and $R^{14}$ are each a $C_1$–$C_{10}$-alkyl group, $M^2$ is carbon, $R^{11}$ and $R^{12}$ are identical or different and $R^{11}$ is a hydrogen atom, a $C_1$–$C_{10}$-group, and $R^{12}$ is a hydrogen atom and at least one of the radicals $R^3$, $R^5$, $R^6$, $R^7$ and $R^9$ is not hydrogen and/or $R^8$ is hydrogen.

3. A stereorigid metallocene compound of the formula I as claimed in claim 1 wherein $M^1$ is zirconium, $R^1$ and $R^2$ are identical and are each a halogen atom, $R^3$, $R^4$, $R^5$, $R^6$, $R^7$ and $R^9$ are identical or different and are each a hydrogen atom or a $C_1$–$C_4$-alkyl group, or a $C_6$–$C_{14}$-aryl group, $R^3$ and $R^4$ and/or $R^5$ and $R^6$ together with the atoms connecting them form an aromatic hydrocarbon ring system having from 4 to 20 carbon atoms, which may in turn be substituted, $R^8$ is a hydrogen atom, $M^2$ is a carbon atom, $R^{10}$, $R^{13}$ and $R^{14}$ are each a $C_1$–$C_6$-alkyl group, and $R^{11}$ and $R^{12}$ are identical and are each a hydrogen atom.

4. The stereorigid metallocene compound as claimed in claim 1, wherein $R^1$ and $R^2$ are identical or different and are each a hydrogen atom, a $C_1$–$C_{10}$-alkyl, $C_1$–$C_{10}$-alkoxy, $C_6$–$C_{10}$-aryl, $C_6$–$C_{25}$-aryloxy, $C_2$–$C_{10}$-alkenyl, $C_7$–$C_{40}$-arylalkyl, $C_7$–$C_{40}$-arylalkenyl group, an OH group, a halogen atom or $NR^{15}_2$, where $R^{15}$ is a halogen atom, a $C_1$–$C_{10}$-alkyl group or a $C_6$–$C_{10}$-aryl group, or $R^1$ and $R^2$, $R^3$, $R^4$, $R^5$, $R^6$, $R^7$, $R^8$, and $R^9$ are identical or different and are each a hydrogen atom, a halogen atom, a $C_1$–$C_{10}$-alkyl group, which is optionally halogenated, a $C_6$–$C_{30}$-aryl group which is optionally halogenated, a $C_6$–$C_{20}$-aryloxy group, $C_2$–$C_{12}$-alkenyl, $C_7$–$C_{40}$-arylalkyl, $C_7$–$C_{40}$-alkylaryl, $C_8$–$C_{40}$-arylalkenyl group, and —$SiR^{15}_3$, —$NR^{15}_2$, —$SiOR^{15}_3$, —$SiSR^{15}_3$ or —$PR^{15}_2$ radical, where $R^{15}$ are identical or different and are each a halogen atom, a $C_1$–$C_{10}$-alkyl group or a $C_6$–$C_{10}$-aryl group or form a ring system, or two or more adjacent radicals $R^3$, $R^4$, $R^5$, $R^6$, $R^7$, $R^8$ and $R^9$ together with the atoms connecting them form a ring system which contains 4 to 40 carbon atoms, $R^{10}$, $R^{13}$ and $R^{14}$ are identical and $R^{11}$ and $R^{12}$ are identical or different and each are a hydrogen atom, a $C_1$–$C_{20}$-alkyl which optionally is halogenated, a $C_1$–$C_{10}$-alkoxy group which is optionally halogenated, a $C_6$–$C_{20}$-aryl group which is optionally halogenated, a $C_2$–$C_{12}$-alkenyl group which is optionally halogenated, a $C_7$–$C_{40}$-arylalkyl group which is optionally, halogenated a $C_7$–$C_{40}$-alkylaryl group which is optionally halogenated, —$NR^{15}_3$, —$SR^{15}_2$, —$SiR^{15}_3$ or —$OSiR^5_3$, where $R^{15}$ is a halogen atom, a $C_1$–$C_{10}$-alkyl group or a $C_6$–$C_{10}$-aryl group.

5. The stereorigid metallocene compound as claimed in claim 4 wherein $R^3$, $R^4$, $R^5$, $R^6$, $R^7$, $R^8$, $R^9$ together with the atoms connecting them form a ring system which contains 6 to 20 carbon atoms.

6. The stereorigid metallocene compound as claimed in claim 2, wherein $M^1$ is titanium, zirconium or hafnium and $R^1$ and $R^2$ are identical and are each a fluorine, chlorine, bromine or iodine and $R^{10}$, $R^{13}$ and $R^{14}$ are each a $C_1$–$C_6$-alkyl group, $R^{11}$ is a hydrogen atom or a $C_1$–$C_4$-alkyl group or a $C_6$–$C_{10}$-aryl group.

7. The stereorigid metallocene as claimed in claim 6, wherein $M^1$ is zirconium, $R^1$ and $R^2$ are chlorine a $R^{10}$, $R^{13}$ and $R^{14}$ are each a $C_1$–$C_6$-alkyl group.

8. The stereorigid metallocene as claimed in claim 3 wherein $R^1$ and $R^2$ are chlorine, $R^3$, $R^4$, $R^5$, $R^6$, $R^7$ and $R^9$ are identical or different and are each a hydrogen atom, methyl, ethyl, propyl, isopropyl, butyl, isobutyl, phenyl or naphthyl, or $R^3$ and $R^4$ and/or $R^5$ and $R^6$ together with the atoms connecting them form an aromatic hydrocarbon ring system which may in turn be substituted, and $R^{10}$, $R^{13}$ and $R^{14}$ are each a methyl.

9. The stereorigid metallocene compound as claimed in claim 1, wherein the compound of formula I is selected from the group consisting of

[4-($\eta^5$-cyclopentadienyl)-4,6,6-trimethyl-($\eta^5$-4,5-tetrahydropentalene)]-dichlorotitanium,

[4-($\eta^5$-cyclopentadienyl)-4,6,6-trimethyl-($\eta^5$-4,5-tetrahydropentalene)]-dichlorozirconium,

[4-($\eta^5$-cyclopentadienyl)-4,6,6-trimethyl-($\eta^5$-4,5-tetrahydropentalene)]-dichlorohafnium,

[4-($\eta^5$-3'-methylcyclopentadienyl)-4,6,6-trimethyl-($\eta^5$-4,5-tetrahydropentalene)]dichlorozirconium,

[4-($\eta^5$-3'-ethylcyclopentadienyl)-4,6,6-trimethyl-($\eta^5$-4,5-tetrahydropentalene)]dichlorozirconium,

[4-($\eta^5$-3'-isopropylcyclopentadienyl)-4,6,6-trimethyl-($\eta^5$-4,5-tetrahydropentalene)]dichlorozirconium,

[4-($\eta^5$-3'-isobutylcyclopentadienyl)-4,6,6-trimethyl-($\eta^5$-4,5-tetrahydropentalene)]dichlorozirconium,

[4-($\eta^5$-3'-cyclohexylcyclopentadienyl)-4,6,6-trimethyl-($\eta^5$-4,5-tetrahydropentalene)]dichlorozirconium,

[4-($\eta^5$-3'-tert-butylcyclopentadienyl)-4,6,6-trimethyl-($\eta^5$-4,5-tetrahydropentalene)]dichlorozirconium,

[4-($\eta^5$-3'-benzylcyclopentadienyl)-4,6,6-trimethyl-($\eta^5$-4,5-tetrahydropentalene)]dichlorozirconium,

[4-($\eta^5$-3'-phenylcyclopentadienyl)-4,6,6-trimethyl-($\eta^5$-4,5-tetrahydropentalene)]dichlorozirconium,

[4-($\eta^5$-3'-trimethylsilylcyclopentadienyl)-4,6,6-trimethyl-($\eta^5$-4,5-tetrahydropentalene)]dichlorozirconium,

[4-($\eta^5$-3'-methyl-5'-methylcyclopentadienyl)-4,6,6-trimethyl-($\eta^5$-4,5-tetrahydropentalene)]dichlorozirconium,

[4-($\eta^5$-3'-ethyl-5'-methylcyclopentadienyl)-4,6,6-trimethyl-($\eta^5$-4,5-tetrahydropentalene)]dichlorozirconium,

[4-($\eta^5$-3'-isopropyl-5'-methylcyclopentadienyl)-4,6,6-trimethyl-($\eta^5$-4,5-tetrahydropentalene)]dichlorozirconium,

[4-($\eta^5$-3'-tert-butyl-5'-methylcyclopentadienyl)-4,6,6-trimethyl-($\eta^5$-4,5-tetrahydropentalene)]dichlorozirconium,

[4-($\eta^5$-3'-benzyl-5'-methylcyclopentadienyl)-4,6,6-trimethyl-($\eta^5$-4,5-tetrahydropentalene)]dichlorozirconium,

[4-($\eta^5$-3'-phenyl-5'-methylcyclopentadienyl)-4,6,6-trimethyl-($\eta^5$-4,5-tetrahydropentalene)]dichlorozirconium,

[4-($\eta^5$-3'-methyl-5'-ethylcyclopentadienyl)-4,6,6-trimethyl-($\eta^5$-4,5-tetrahydropentalene)]dichlorozirconium,

[4-($\eta^5$-3'-ethyl-5'-ethylcyclopentadienyl)-4,6,6-trimethyl-($\eta^5$-4,5-tetrahydropentalene)]dichlorozirconium,

[4-($\eta^5$-3'-isopropyl-5'-ethylcyclopentadienyl)-4,6,6-trimethyl-($\eta^5$-4,5-tetrahydropentalene)]dichlorozirconium,

[4-($\eta^5$-3'-tert-butyl-5'-ethylcyclopentadienyl)-4,6,6-trimethyl-($\eta^5$-4,5-tetrahydropentalene)]dichlorozirconium,

[4-($\eta^5$-3'-benzyl-5'-ethylcyclopentadienyl)-4,6,6-trimethyl-($\eta^5$-4,5-tetrahydropentalene)]dichlorozirconium,

[4-($\eta^5$-3'-phenyl-5'-ethylcyclopentadienyl)-4,6,6-trimethyl-($\eta^5$-4,5-tetrahydropentalene)]dichlorozirconium,

[4-($\eta^5$-3'-methyl-5'-isopropylcyclopentadienyl)-4,6,6-trimethyl-($\eta^5$-4,5-tetrahydropentalene)]dichlorozirconium,

[4-($\eta^5$-3'-ethyl-5'-isopropylcyclopentadienyl)-4,6,6-trimethyl-($\eta^5$-4,5-tetrahydropentalene)]dichlorozirconium,

[4-($\eta^5$-3'-isopropyl-5'-isopropylcyclopentadienyl)-4,6,6-trimethyl-($\eta^5$-4,5-tetrahydropentalene)]dichlorozirconium,

[4-($\eta^5$-3'-tert-butyl-5'-isopropylcyclopentadienyl)-4,6,6-trimethyl-($\eta^5$-4,5-tetrahydropentalene)]dichlorozirconium,

[4-($\eta^5$-3'-benzyl-5'-isopropylcyclopentadienyl)-4,6,6-trimethyl-($\eta^5$-4,5-tetrahydropentalene)]dichlorozirconium,

[4-($\eta^5$-3'-phenyl-5'-isopropylcyclopentadienyl)-4,6,6-trimethyl-($\eta^5$-4,5-tetrahydropentalene)]dichlorozirconium,

[4-($\eta^5$-cyclopentadienyl)-4,6,6-triethyl-($\eta^5$-4,5-tetrahydropentalene)]dichlorozirconium,

[4-($\eta^5$-3'-methylcyclopentadienyl)-4,6,6-triethyl-($\eta^5$-4,5-tetrahydropentalene)]dichlorozirconium,

[4-($\eta^5$-3'-ethylcyclopentadienyl)-4,6,6-triethyl-($\eta^5$-4,5-tetrahydropentalene)]dichlorozirconium,

[4-($\eta^5$-3'-isopropylcyclopentadienyl)-4,6,6-triethyl-($\eta^5$-4,5-tetrahydropentalene)]dichlorozirconium,

[4-($\eta^5$-3'-isobutylcyclopentadienyl)-4,6,6-triethyl-($\eta^5$-4,5-tetrahydropentalene)]dichlorozirconium,

[4-($\eta^5$-3'-cyclohexylcyclopentadienyl)-4,6,6-triethyl-($\eta^5$-4,5-tetrahydropentalene)]dichlorozirconium,

[4-($\eta^5$-3'-tert-butylcyclopentadienyl)-4,6,6-triethyl-($\eta^5$-4,5-tetrahydropentalene)]dichlorozirconium,

[4-($\eta^5$-3'-benzylcyclopentadienyl)-4,6,6-triethyl-($\eta^5$-4,5-tetrahydropentalene)]dichlorozirconium,

[4-($\eta^5$-3'-phenylcyclopentadienyl)-4,6,6-triethyl-($\eta^5$-4,5-tetrahydropentalene)]dichlorozirconium,

[4-($\eta^5$-cyclopentadienyl)-4-methyl-6,6-diethyl-($\eta^5$-4,5-tetrahydropentalene)]dichlorozirconium,

[4-($\eta^5$-3'-methylcyclopentadienyl)-4-methyl-6,6-diethyl-($\eta^5$-4,5-tetrahydropentalene)]dichlorozirconium,

[4-($\eta^5$-3'-ethylcyclopentadienyl)-4-methyl-6,6-diethyl-($\eta^5$-4,5-tetrahydropentalene)]dichlorozirconium,

[4-($\eta^5$-3-isopropylcyclopentadienyl)-4-methyl-6,6-diethyl-($\eta^5$-4,5-tetrahydropentalene)]dichlorozirconium,

[4-($\eta^5$-3'-benzylcyclopentadienyl)-4-methyl-6,6-diethyl-($\eta^5$-4,5-tetrahydropentalene)]dichlorozirconium,

[4-($\partial^5$-3'-phenylcyclopentadienyl)-4-methyl6,6-diethyl-($\eta^5$-4,5-tretrahydropentalene)]dichlorozirconium,

[4-($\eta^5$-cyclopentadienyl)-4-ethyl-6,6-dimethyl-($\eta^5$-4,5-tetrahydropentalene)]dichlorozirconium,

[4-($\eta^5$-3'-methylcyclopentadienyl)-4-ethyl-6,6-dimethyl-($\eta^5$-4,5-tetrahydropentalene)]dichlorozirconium,

[4-($\eta^5$-3'-ethylcyclopentadienyl)-4-ethyl-6,6-dimethyl-($\eta^5$-4,5-tetrahydropentalene)]dichlorozirconium,

[4-($\eta^5$-3'-isopropylcyclopentadienyl)-4-ethyl-6,6-dimethyl-($\eta^5$-4,5-tetrahydropentalene)]dichlorozirconium,

[4-($\eta^5$-3'-benzylcyclopentadienyl)-4-ethyl-6,6-dimethyl-($\eta^5$-4,5-tetrahydropentalene)]dichlorozirconium,

[4-($\eta^5$-3'-phenylcyclopentadienyl)-4-ethyl-6,6-dimethyl-($\eta^5$-4,5-tetrahydropentalene)]dichlorozirconium,

[4-($\eta^5$-cyclopentadienyl)-4-methyl-6-ethyl-6-methyl-($\eta^5$-4,5-tetrahydropentalene)]dichlorozirconium,

[4-($\eta^5$-3'-methylcyclopentadienyl)-4-methyl-6-ethyl-6-methyl-($\eta^5$-4,5-tetrahydropentalene)]dichlorozirconium,

[4-($\eta^5$-3'-ethylcyclopentadienyl)-4-methyl-6-ethyl-6-methyl-($\eta^5$-4,5-tetrahydropentalene)]dichlorozirconium,

[4-($\eta^5$-3'-isopropylcyclopentadienyl)-4-methyl-6-ethyl-6-methyl-($\eta^5$-4,5-tetrahydropentalene)]dichlorozirconium,

[4-($\eta^5$-3'-benzylcyclopentadienyl)-4-methyl-6-ethyl-6-methyl-($\eta^5$-4,5-tetrahydropentalene)]dichlorozirconium,

[4-($\eta^5$-3'-phenylcyclopentadienyl)-4-methyl-6-ethyl-6-methyl-($\eta^5$-4,5-tetrahydropentalene)]dichlorozirconium,

[4-($\eta^5$-cyclopentadienyl)-4-methyl-6-isopropyl-6-methyl-($\eta^5$-4,5-tetrahydropentalene)]dichlorozirconium,

[4-($\eta^5$-3'-methylcyclopentadienyl)-4-methyl-6-isopropyl-6-methyl-($\eta^5$-4,5-tetrahydropentalene)]dichlorozirconium,

[4-($\eta^5$-3'-ethylcyclopentadienyl)-4-methyl-6-isopropyl-6-methyl-($\eta^5$-4,5-tetrahydropentalene)]dichlorozirconium,
[4-($\eta^5$-3'-isopropylcyclopentadienyl)-4-methyl-6-isopropyl-6-methyl-($\eta^5$-4,5-tetrahydropentalene)]dichlorozirconium,
[4-($\eta^5$-3'-benzylcyclopentadienyl)-4-methyl-6-isopropyl-6-methyl-($\eta^5$-4,5-tetrahydropentalene)]dichlorozirconium,
[4-($\eta^5$-3'-phenylcyclopentadienyl)-4-methyl-6-isopropyl-6-methyl-($\eta^5$-4,5-tetrahydropentalene)]dichlorozirconium,
[4-($\eta^5$-3'-trimethylsilyl-5'-ethylcyclopentadienyl)-4,6,6-trimethyl-($\eta^5$-4,5-tetrahydropentalene)]dichlorozirconium,
[4-($\eta^5$-3'-trimethylsilyl-5'-isopropylcyclopentadienyl)-4,6,6-trimethyl-($\eta^5$-4,5-tetrahydropentalene)]dichlorozirconium,
[4-($\eta^5$-3'-trimethylsilylcyclopentadienyl)-4,6,6-triethyl-($\eta^5$-4,5-tetrahydropentalene)]dichlorozirconium,
[4-($\eta^5$-3'-trimethylsilylcyclopentadienyl)-4-methyl-6,6-diethyl-($\eta^5$-4,5-tetrahydropentalene)]dichlorozirconium,
[4-($\eta^5$-3'-trimethylsilylcyclopentadienyl)-4-ethyl-6,6-dimethyl-($\eta^5$-4,5-tetrahydropentalene)]dichlorozirconium,
[4-($\eta^5$-3'-trimethylsilylcyclopentadienyl)-4-methyl-6-ethyl-6-methyl-($\eta^5$-4,5-tetrahydropentalene)]dichlorozirconium,
[4-($\eta^5$-3'-trimethylsilylcyclopentadienyl)-4-methyl-6-isopropyl-6-methyl-($\eta^5$-4,5-tetrahydropentalene)]dichlorozirconium,
[4-($\eta^5$-fluorenyl)-2,4,6,6-tetramethyl-$\eta^5$-tetrahydropentalene]dichlorozirconium,
[4-($\eta^5$-fluorenyl)-2,4,6,6-tetramethyl-$\eta^5$-tetrahydropentalene]dichlorotitanium,
[4-($\eta^5$-fluorenyl)-2,4,6,6-tetramethyl-$\eta^5$-tetrahydropentalene]dichlorohafnium,
[4-($\eta^5$-fluorenyl)-2,4,6,6-tetramethyl-$\eta^5$-tetrahydropentalene]-bis(diethylamino)zirconium,
[4-($\eta^5$-fluorenyl)-2,4,6,6-tetramethyl-$\eta^5$-tetrahydropentalene]-bis(dimethylamino)zirconium,
[4-($\eta^5$-fluorenyl)-4,6,6-trimethyl-(2-ethyl)-$\eta^5$-tetrahydropentalene]-dichlorozirconium,
[4-($\eta^5$-fluorenyl)-4,6,6-trimethyl-(2-isopropyl)-$\eta^5$-tetrahydropentalene]-dichlorozirconium,
[4-($\eta^5$-fluorenyl)-4,6,6-trimethyl-(2-benzyl)-$\eta^5$-tetrahydropentalene]-dichlorozirconium,
[4-($\eta^5$-fluorenyl)-4,6,6-trimethyl-(2-trimethylsilyl)-$\eta^5$-tetrahydropentalene]-dichlorozirconium,
[4-($\eta^5$-indenyl)-2,4,6,6-tetramethyl-$\eta^5$-tetrahydropentalene]-dichlorozirconium,
[4-($\eta^5$-indenyl)-2,4,6,6-tetramethyl-$\eta^5$-tetrahydropentalene]dichlorotitanium,
[4-($\eta^5$-indenyl)-2,4,6,6-tetramethyl-$\eta^5$-tetrahydropentalene]dichlorohafnium,
[4-($\eta^5$-indenyl)-2,4,6,6-tetramethyl-$\eta^5$-tetrahydropentalene]bis(diethylamino)zirconium,
[4-($\eta^5$-indenyl)-2,4,6,6-tetramethyl-$\eta^5$-tetrahydropentalene]bis(dimethylamino)zirconium,
[4-($\eta^5$-indenyl)-4,6,6-trimethyl-(2-ethyl)-$\eta^5$-tetrahydropentalene]dichlorozirconium,
[4-($\eta^5$-indenyl)-4,6,6-trimethyl-(2-isopropyl)-$\eta^5$-tetrahydropentalene]dichlorozirconium,
[4-($\eta^5$-indenyl)-4,6,6-trimethyl-(2-benzyl)-$\eta^5$-tetrahydropentalene]dichlorozirconium,
[4-($\eta^5$-indenyl)-4,6,6-trimethyl-(2-trimethylsilyl)-$\eta^5$-tetrahydropentalene]dichlorozirconium,
[4-($\eta^5$-2-methylindenyl)-2,4,6,6-tetramethyl-$\eta^5$-tetrahydropentalene]-dichlorozirconium,
[4-($\eta^5$-2-methylindenyl)-2,4,6,6-tetramethyl-$\eta^5$-tetrahydropentalene]-dichlorotitanium,
[4-($\eta^5$-2-methylindenyl)-2,4,6,6-tetramethyl-$\eta^5$-tetrahydropentalene]-dichlorohafnium,
[4-($\eta^5$-2-methylindenyl)-2,4,6,6-tetramethyl-$\eta^5$-tetrahydropentalene]bis(diethylamino)zirconium,
[4-($\eta^5$-2-methylindenyl)-2,4,6,6-tetramethyl-$\eta^5$-tetrahydropentalene]bis(diethylamino)zirconium,
[4-($\eta^5$-2-methylindenyl)-4,6,6-trimethyl-(2-ethyl)-$\eta^5$-tetrahydropentalene]dichlorozirconium,
[4-($\eta^5$-2-methylindenyl)-4,6,6-trimethyl-(2-isopropyl)-$\eta^5$-tetrahydropentalene]dichlorozirconium,
[4-($\eta^5$-2-methylindenyl)-4,6,6-trimethyl-(2-benzyl)-$\eta^5$-tetrahydropentalene]dichlorozirconium,
[4-($\eta^5$-2-methylindenyl)-4,6,6-trimethyl-(2-trimethylsilyl)-$\eta^5$-tetrahydropentalene]dichlorozirconium,
[4-($\eta^5$-benzoindenyl)-2,4,6,6-tetramethyl-$\eta^5$-tetrahydropentalene]dichlorozirconium,
[4-($\eta^5$-benzoindenyl)-2,4,6,6-tetramethyl-$\eta^5$-tetrahydropentalene]dichlorotitanium,
[4-($\eta^5$-benzoindenyl)-2,4,6,6-tetramethyl-$\eta^5$-tetrahydropentalene]dichlorohafnium,
[4-($\eta^5$-benzoindenyl)-2,4,6,6-tetramethyl-$\eta^5$-tetrahydropentalene]bis(diethylamino)zirconium,
[4-($\eta^5$-benzoindenyl)-2,4,6,6-tetramethyl-$\eta^5$-tetrahydropentalene]bis(dimethylamino)zirconium,
[4-($\eta^5$-benzoindenyl)-4,6,6-trimethyl(2-ethyl)-$\eta^5$-tetrahydropentalene]-dichlorozirconium,
[4-($\eta^5$-benzoindenyl)-4,6,6-trimethyl-(2-isopropyl)-$\eta^5$-tetrahydropentalene]-dichlorozirconium,
[4-($\eta^5$-benzoindenyl)-4,6,6-trimethyl-(2-benzyl)-$\eta^5$-tetrahydropentalene]-dichlorozirconium,
[4-($\eta^5$-benzoindenyl)-4,6,6-trimethyl-(2-trimethylsilyl)-$\eta^5$-tetrahydropentalene]-dichlorozirconium,
[4-($\eta^5$-cyclopentadienyl)-2,4,6,6-tetramethyl-$\eta^5$-tetrahydropentalene]-dichlorozirconium,
[4-($\eta^5$-cyclopentadienyl)-2,4,6,6-tetramethyl-$\eta^5$-tetrahydropentalene]-dichlorotitanium,
[4-($\eta^5$-cyclopentadienyl)-2,4,6,6-tetramethyl-$\eta^5$-tetrahydropentalene]-dichlorohafnium,
[4-($\eta^5$-cyclopentadienyl)-2,4,6,6-tetramethyl-$\eta^5$-tetrahydropentalene]-bis(diethylamino)zirconium,
[4-($\eta^5$-cyclopentadienyl)-2,4,6,6-tetramethyl-$\eta^5$-tetrahydropentalene]-bis(dimethylamino)zirconium,
[4-($\eta^5$-cyclopentadienyl)-4,6,6-trimethyl-(2-ethyl)-$\eta^5$-tetrahydropentalene]-dichlorozirconium,
[4-($\eta^5$-cyclopentadienyl)-4,6,6-trimethyl-(2-isopropyl)-$\eta^5$-tetrahydropentalene]dichlorozirconium,
[4-($\eta^5$-cyclopentadienyl)-4,6,6-trimethyl-(2-benzyl)-$\eta^5$-tetrahydropentalene]dichlorozirconium,
[4-($\eta^5$-cyclopentadienyl)-4,6,6-trimethyl-(2-trimethylsilyl)-$\eta^5$-tetrahydropentalene]dichlorozirconium,
[4-($\eta^5$-fluorenyl)-2,4-dimethyl-6-phenyl-($\eta^5$-4,5-tetrahydropentalene)]-dichlorozirconium,
[4-($\eta^5$-fluorenyl)-2-ethyl-4-methyl-6-phenyl-($\eta^5$-4,5-tetrahydropentalene)]-dichlorozirconium,
[4-($\eta^5$-fluorenyl)-2-isopropyl-4-methyl-6-phenyl-($\eta^5$-4,5-tetrahydropentalene)]dichlorozirconium,
[4-($\eta^5$-fluorenyl)-2-tert-butyl-4-methyl-6-phenyl-($\eta^5$-4,5-tetrahydropentalene)]dichlorozirconium,
[4-($\eta^5$-fluorenyl)-2-benzyl-4-methyl-6-phenyl-($\eta^5$-4,5-tetrahydropentalene)]dichlorozirconium,
[4-($\eta^5$-fluorenyl)-2-trimethylsilyl-4-methyl-6-phenyl-($\eta^5$-4,5-tetrahydropentalene)]dichlorozirconium,
[4-($\eta^5$-fluorenyl)-2-dimethyl-6-o-anisyl-($\eta^5$-4,5-tetrahydropentalene)]dichlorozirconium,
[4-($\eta^5$-fluorenyl)-2-ethyl-4-methyl-6-o-anisyl-($\eta^5$-4,5-tetrahydropentalene)]dichlorozirconium,
[4-($\eta^5$-fluorenyl)-2-isopropyl-4-methyl-o-anisyl-($\eta^5$-4,5-tetrahydropentalene)]dichlorozirconium,

[4-($\eta^5$-fluorenyl)-2-tert-butyl-4-methyl-6-o-anisyl-($\eta^5$-4,5-tetrahydropentalene)]dichlorozirconium,
[4-($\eta^5$-fluorenyl)-2-benzyl-4-methyl-6-o-anisyl-($\eta^5$-4,5-tetrahydropentalene)]dichlorozirconium,
[4-($\eta^5$-fluorenyl)-2-trimethylsilyl-4-methyl-6-o-anisyl-($\eta^5$-4,5-tetrahydropentalene)]dichlorozirconium,
[4-($\eta^5$-fluorenyl)-2-methyl-4,6-diphenyl-($\eta^5$-4,5-tetrahydropentalene)]dichlorozirconium,
[4-($\eta^5$-fluorenyl)-2-ethyl-4,6-diphenyl-($\eta^5$-4,5-tetrahydropentalene)]dichlorozirconium,
[4-($\eta^5$-fluorenyl)-2-isopropyl-4,6-diphenyl-($\eta^5$-4,5-tetrahydropentalene)]dichlorozirconium,
[4-($\eta^5$-fluorenyl)-2-tert-butyl-4,6-diphenyl-($\eta^5$-4,5-tetrahydropentalene)]dichlorozirconium,
[4-($\eta^5$-fluorenyl)-2-benzyl-4,6-diphenyl-($\eta^5$-4,5-tetrahydropentalene)]dichlorozirconium,
[4-($\eta^5$-fluorenyl)-2-trimethylsilyl-4,6-diphenyl-($\eta^5$-4,5-tetrahydropentalene)]dichlorozirconium,
[4-($\eta^5$-fluorenyl)-2,4-dimethyl-6-p-tolyl-($\eta^5$-4,5-tetrahydropentalene)]dichlorozirconium,
[4-($\eta^5$-fluorenyl)-2,4-ethyl-4-methyl-6-p-tolyl-($\eta^5$-4,5-tetrahydropentalene)]dichlorozirconium,
[4-($\eta^5$-fluorenyl)-2-isopropyl-4-methyl-6-p-tolyl-($\eta^5$-4,5-tetrahydropentalene)]dichlorozirconium,
[4-($\eta^5$-fluorenyl)-2-tert-butyl-4-methyl-p-tolyl-($\eta^5$-4,5-tetrahydropentalene)]dichlorozirconium,
[4-($\eta^5$-fluorenyl)-2-benzyl-4-methyl-6-p-tolyl-($\eta^5$-4,5-tetrahydropentalene)]dichlorozirconium,
[4-($\eta^5$-fluorenyl)-2-trimethylsilyl-4-methyl-6-p-tolyl-($\eta^5$-4,5-tetrahydropentalene)]dichlorozirconium,
[4-($\eta^5$-fluorenyl)-2,4-dimethyl-6-naphthyl-($\eta^5$-4,5-tetrahydropentalene)]dichlorozirconium,
[4-($\eta^5$-fluorenyl)-2-ethyl-4-methyl-6-naphthyl-($\eta^5$-4,5-tetrahydropentalene)]dichlorozirconium,
[4-($\eta^5$-fluorenyl)-2-isopropyl-4-methyl-6-naphthyl-($\eta^5$-4,5-tetrahydropentalene)]dichlorozirconium,
[4-($\eta^5$-fluorenyl)-2-tert-butyl-4-methyl-6-naphthyl-($\eta^5$-4,5-tetrahydropentalene)]dichlorozirconium,
[4-($\eta^5$-fluorenyl)-2-benzyl-4-methyl-6-naphthyl-($\eta^5$-4,5-tetrahydropentalene)]dichlorozirconium,
[4-($\eta^5$-fluorenyl)-2-trimethylsilyl-4-methyl-6-naphthyl-($\eta^5$-4,5-tetrahydropentalene]dichlorozirconium,
[4-($\eta^5$-fluorenyl)-2,4-dimethyl-6-phenyl-($\eta^5$-4,5-tetrahydropentalene)]dichlorotitanium,
[4-($\eta^5$-fluorenyl)-2,4-dimethyl-6-phenyl-($\eta^5$-4,5-tetrahydropentalene)]dichlorohafnium and
[4-($\eta^5$-fluorenyl)-2,4-dimethyl-6-phenyl-($\eta^5$-4,5-tetrahydropentalene)]bis(diethylamino)zirconium.

* * * * *